(12) United States Patent
Hirata et al.

(10) Patent No.: US 10,980,582 B2
(45) Date of Patent: Apr. 20, 2021

(54) LOCKING PLATE SYSTEM FOR TREATMENT OF DISTAL RADIUS FRACTURE

(71) Applicants: National University Corporation Nagoya University, Aichi (JP); Nipro Corporation, Osaka (JP)

(72) Inventors: Hitoshi Hirata, Aichi (JP); Tatsuya Hara, Aichi (JP); Hidemasa Yoneda, Aichi (JP); Shunichi Bandoh, Gifu (JP)

(73) Assignees: NIPRO CORPORATION, Osaka (JP); NATIONAL UNIVERSITY CORPORATION NAGOYA UNIVERSITY, Aichi (JP)

( * ) Notice: Subject to any disclaimer, the term of this patent is extended or adjusted under 35 U.S.C. 154(b) by 508 days.

(21) Appl. No.: 15/324,331

(22) PCT Filed: Jul. 9, 2015

(86) PCT No.: PCT/JP2015/069756
§ 371 (c)(1),
(2) Date: May 2, 2017

(87) PCT Pub. No.: WO2016/006653
PCT Pub. Date: Jan. 14, 2016

(65) Prior Publication Data
US 2017/0231673 A1      Aug. 17, 2017

(30) Foreign Application Priority Data

Jul. 9, 2014   (JP) .............................. JP2014-141511

(51) Int. Cl.
*A61B 17/80* (2006.01)
*A61B 17/68* (2006.01)
(Continued)

(52) U.S. Cl.
CPC .......... *A61B 17/8057* (2013.01); *A61B 17/68* (2013.01); *A61B 17/8028* (2013.01);
(Continued)

(58) Field of Classification Search
CPC ............ A61B 17/8085; A61B 17/8023; A61B 17/8047; A61B 17/80; A61B 17/8061;
(Continued)

(56) References Cited

U.S. PATENT DOCUMENTS 6,221,073 B1 *   4/2001   Weiss .................  A61B 17/8061
                                                       606/281
6,712,820 B2     3/2004   Orbay
(Continued)

FOREIGN PATENT DOCUMENTS

GB         2405342       3/2005
JP         2007-21001    2/2007
(Continued)

OTHER PUBLICATIONS

Acumed LLC. ACU-LOC Wrist Plating System. Apr. 2012, intermedic. com.br/files/downloads/HNW00-01-D_Acu-Loc_SurgicalTech. pdf, visited on Apr. 12, 2019 (Year: 2012).*
(Continued)

*Primary Examiner* — Marcela I. Shirsat
(74) *Attorney, Agent, or Firm* — McDonnell Boehnen Hulbert & Berghoff LLP

(57) ABSTRACT

Provided is a locking plate system for treatment of a distal radius fracture including a locking plate (4) that is a flat laminate of intermediate molding materials that includes carbon fibers as a reinforcing material and thermoplastic resin as a matrix; a screw anchor (5) having a shaft portion (10) which has a principal thread (13) achieving a self-tapping action formed thereon and an outer circumference of a head portion of the screw anchor (5) which has an auxiliary
(Continued)

thread (13) achieving a self-tapping action tapped thereon; and a through-hole (6) in the radius locking plate (4), which allows the radius main body (3) and the fractured bone piece (2) to be threadably fixed to the radius locking plate (4) and having a diameter that is oversized relative to the principal thread (11), and that is undersized relative to the auxiliary thread (13).

23 Claims, 34 Drawing Sheets

(51) Int. Cl.
*A61B 17/86* (2006.01)
*A61B 17/00* (2006.01)

(52) U.S. Cl.
CPC ...... *A61B 17/8061* (2013.01); *A61B 17/8605* (2013.01); *A61B 17/8625* (2013.01); *A61B 17/8085* (2013.01); *A61B 2017/00526* (2013.01); *A61B 2017/00902* (2013.01)

(58) Field of Classification Search
CPC . A61B 17/8052; A61B 17/8057; A61B 17/68; A61B 17/8605; A61B 17/8625; A61B 2017/00526; A61B 2017/00902; A61B 17/8028
USPC .............................. 606/280, 70–71, 281–299
See application file for complete search history.

(56) References Cited

U.S. PATENT DOCUMENTS

| | | | | |
|---|---|---|---|---|
| 6,786,909 | B1* | 9/2004 | Dransfeld | A61B 17/8052 606/280 |
| 2001/0011172 | A1* | 8/2001 | Orbay | A61B 17/68 606/286 |
| 2004/0260291 | A1 | 12/2004 | Jensen | |
| 2006/0009771 | A1* | 1/2006 | Orbay | A61B 17/8057 606/291 |
| 2006/0235400 | A1 | 10/2006 | Schneider | |
| 2008/0234677 | A1 | 9/2008 | Dahners et al. | |
| 2009/0048605 | A1 | 2/2009 | Yurek | |
| 2011/0218570 | A1 | 9/2011 | Felix et al. | |
| 2012/0059376 | A1* | 3/2012 | Rains | A61B 17/72 606/62 |
| 2013/0184765 | A1* | 7/2013 | Beyar | A61B 17/8052 606/281 |
| 2013/0190829 | A1 | 7/2013 | Batsch et al. | |
| 2014/0066998 | A1 | 3/2014 | Martin | |

FOREIGN PATENT DOCUMENTS

| | | |
|---|---|---|
| WO | WO 2004/107957 | 12/2004 |
| WO | WO 2007/010671 | 1/2007 |
| WO | WO2007/086832 | 8/2007 |
| WO | WO 2007086832 | 8/2007 |
| WO | WO 2009/023666 | 2/2009 |
| WO | WO 2009/058969 | 5/2009 |
| WO | WO 2008/115318 | 9/2009 |
| WO | WO 2010/045473 | 4/2010 |
| WO | WO 2014/072983 | 5/2014 |

OTHER PUBLICATIONS

European Search Report prepared by the European Patent Office in application No. 15818952.2 dated Mar. 5, 2018.
Extended European Search Report prepared by the European Patent Office in application No. 15818952.2 dated Jul. 2, 2018.

* cited by examiner

Fig.1
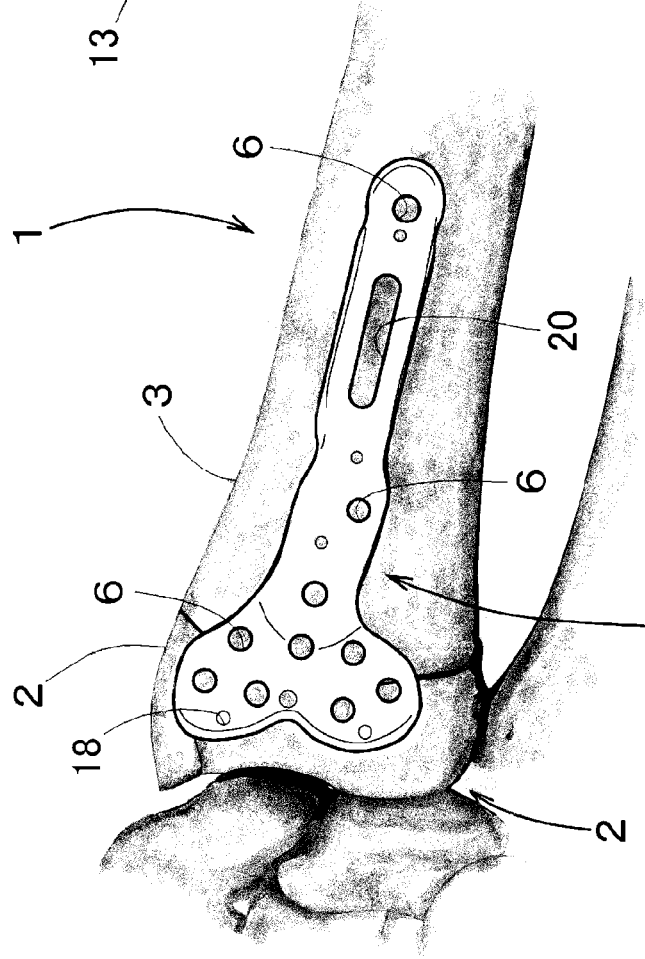
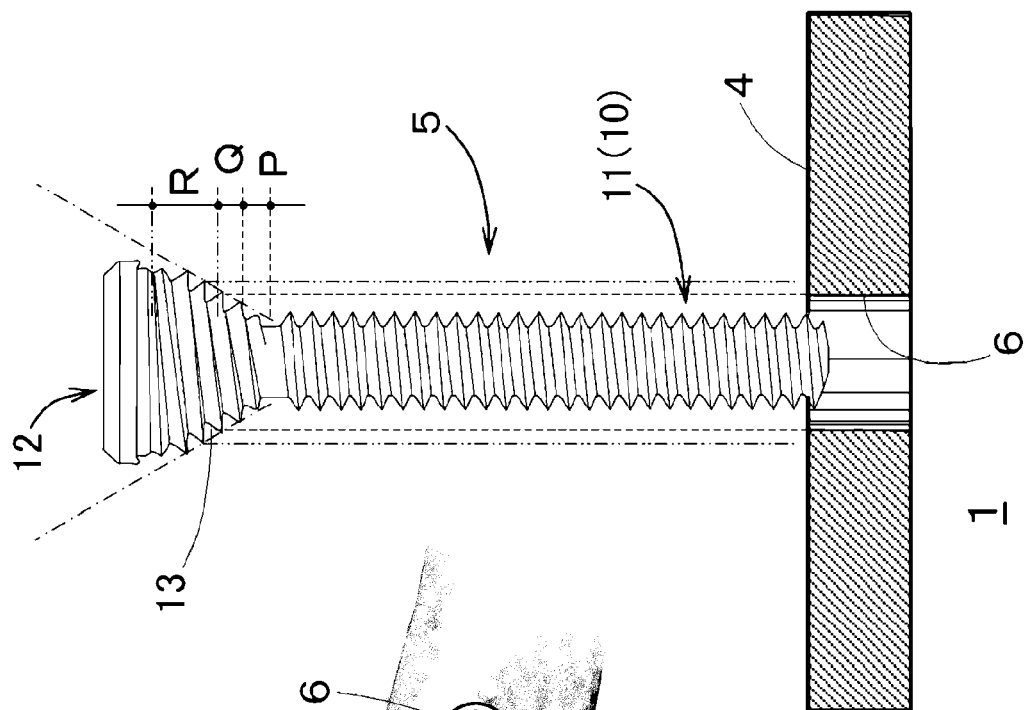

Fig.31
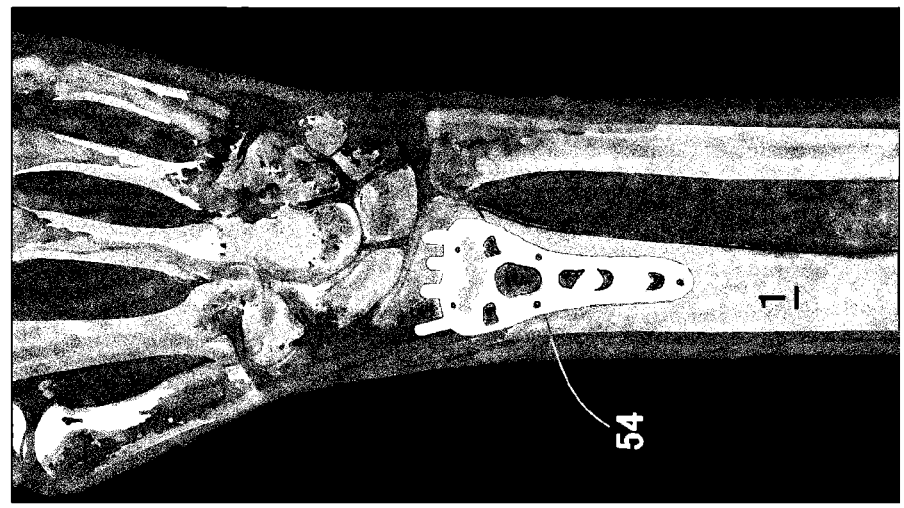
(a)
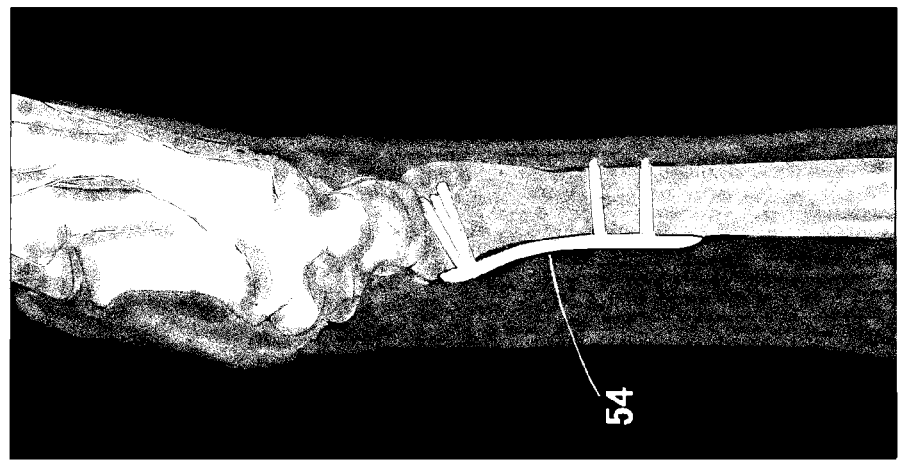
(b)

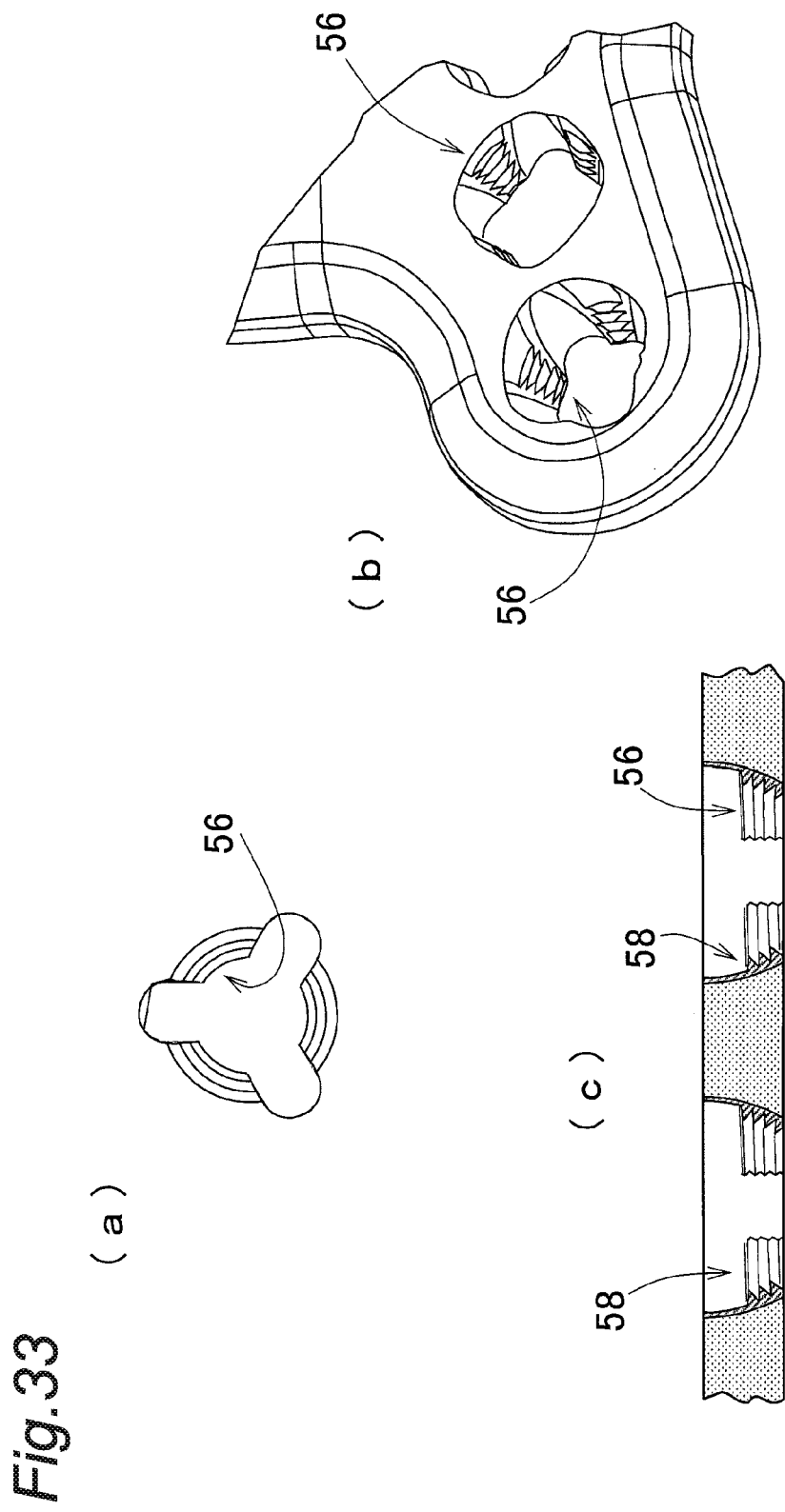

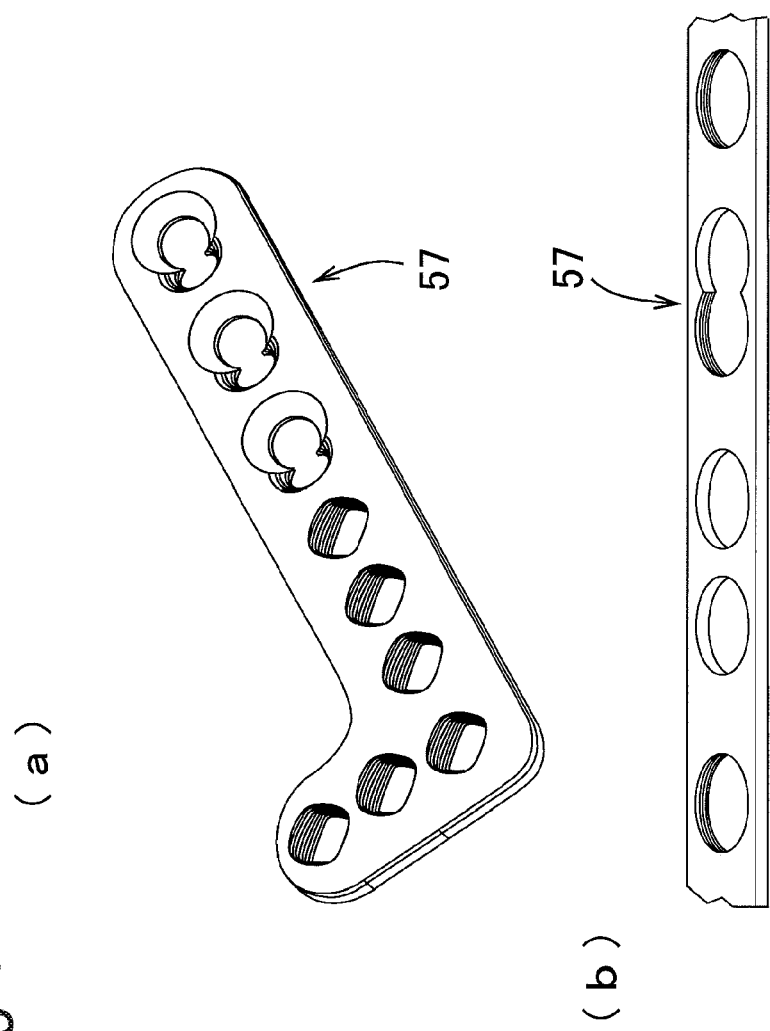

LOCKING PLATE SYSTEM FOR TREATMENT OF DISTAL RADIUS FRACTURE

TECHNICAL FIELD

The present invention relates to a locking plate system for treatment of a distal radius fracture and, more particularly, to a treatment implement system that includes a radius locking plate to be attached as a bridge between a fractured bone piece and a palmer side of a radius main body at the inside of a body, and screw anchors used therefor, to facilitate bone union or healing of the fractured bone piece produced in the distal portion of the radius with the radius main body.

BACKGROUND ART

Typical parts tending to suffer a fracture due to a brittle-bone disease include a humerus, a radius, a vertebrae, and a femur, and fractures of these bones are called "humeral neck fracture", "distal radius fracture", "vertebral fracture", and "femoral neck fracture". When a person falls down due to stumbling or the like, distal radius fractures are caused by a fall on an outstretched hand with the wrist in dorsi-flection or palmar-flexion. A radius is a tubular bone that extends from an elbow to a wrist side by side with an ulna and that has a bone marrow cavity present therein. As depicted in FIG. 29(a), the ulna 51 is positioned on the side of the little finger (on the left) and the radius 1 is positioned on the side of the thumb (on the right).

The distal tip of the ulna has thereon a styloid process that protrudes toward the side of the little finger, and the distal tip of the radius also has thereon a styloid process 52 that protrudes toward the side of the thumb. The radius is somewhat shorter than the ulna while the radius is thicker than the ulna and has a teardrop portion defining recess (which is often referred to as "teardrop recess") 53 depicted in FIG. 29(b) formed on the palmer side due to a protrusion of a lunate bone fossa positioned on side opposite to that of the styloid process. The teardrop constitutes an important portion that functions as a portion to receive a load to the wrist.

The radius extends from the teardrop recess to the diaphysis with a substantially rectangular column-like cross-section, resulting in a complicated shape. Generally, there exists an individual variation in the morphology of bones of a human body and in the same way exists an individual variation in the morphology of teardrop recess 53 as depicted in FIG. 30.

In a surgical operation for a fracture of the distal tip, the attachment of the radius locking plate is not therefore easy for the operator so that it matches its shape of the radius locking plate with the shape of the teardrop recess and the regions in front and in the back thereof. A flexor tendon failure is remarkably highly likely to occur when, on the radius distal tip, a distal portion of the radius locking plate or the vicinity thereof interferes with the thumb flexor tendon that extends close to the palmer side of the distal radius.

The radius locking plate replaces a splint and a cast made of plaster or an FRP (fiber reinforced plastic) that each fix a limb or a joint from the outside of the fracture region. This is a plate to be directly attached to the radius that can be explored through a volar incision at the wrist, and this plate has a length of 5 cm to 6 cm to have a size capable of being implanted in a living body. This plate establishes robust fixation, which also enables early functional recovery.

Titanium, an alloy thereof, or the like that is strong and lightweight, and that is qualified to have high body safety or biocompatibility is used for the radius locking plate to be implanted in a body. When it is attempted to produce the radius locking plate as a custom-made optimal product of metal, a unique molding mold is necessary that is matched with the shape and the size of bones of each individual.

In this manufacturing scenario, significant increase in production cost and lead time are inevitable. The plate is usually produced as a ready-made product to have those of typical sizes lined up, and reduction of the price of the product is thereby facilitated. In a surgical operation, the plate best matching for the individual bone is employed from the line-up, and any individual perfect fitting cannot therefore be expected.

A practice like the above is also executed for a resin plate. Patent Document 1 describes an example of use of PEEK with which the body safety can be secured. During a surgical operation executed under image intensifier (x-ray) control, a metal plate 54 has an advantage that the metal plate 54 can be clearly perceived as depicted in FIG. 31 while the metal plate 54 has a disadvantage that the affected site is hidden thereby. When the resin plate is employed, the X-ray transmits through it, which enables the position and the orientation of a fractured bone piece to be easily perceived and the affected site can therefore be meticulously cared.

The radius locking plate maintains the fracture reduction, and integrally fixes the radius main body and the fractured bone piece to each other through the plate using some screw anchors. The screw anchors each need to be a hard and strong screw anchor that can laterally self-tap the radius that includes the compact cortical bone, and the cancellous bone in the bone marrow cavity. In many cases, the screw anchors are each made of titanium or an alloy thereof similarly to the radius locking plate.

Through-holes each for the screw anchor to advance in the radius are provided in the radius locking plate. When a large portion of the head portion of the screw anchor remains outside the plate, this causes local pressing or local grazing on the flexor tendon. Necessary is at least a head portion receiving part in each of the holes so as to sink the head portion in the through-hole to accommodate the head portion therein and to prevent any falling out of the anchor. This can be coped with by simply forming a stepwise recess while introduction of a thread mechanism is necessary in the lower half portion of the through-hole (hereinafter, referred to as "in-hole thread").

A thread (hereinafter, referred to as "outer circumference thread") to be screw-fixed to the in-hole thread is naturally formed on the outer circumference of the head portion of the screw anchor. Enabled is the block of any falling out of the anchor toward the side of the radius as well as any reverse-falling out toward the palmer side. Examples of this technique are described in Patent Document 2 and Patent Document 3.

The radius locking plate has a thickness of, for example, 2 mm to 3 mm. When the radius locking plate is made of metal, the disposition of the in-hole thread is not impossible at all. It may be desired that the axis line of the screw anchor directed to the point to which the screw anchor is advanced is displaced from or inclined against the axis line of the in-hole thread. In this case, any falling out of the anchor can be avoided when substantial engagement is achieved between the outer circumference thread and the in-hole thread. Some Patent Documents listed below describe the means for the above.

FIG. 32 depicts the state where the enveloping surface of the tooth tips lining on and beneath the outer circumference thread is formed to be a partial spherical surface and the tooth tip enveloping surface of the in-hole thread is also formed to be a partial spherical surface. These examples are described in Patent Document 3 and Patent Document 4. A recess 55 in the center of each of FIGS. 32(a), 32(b), and 32(c) has a petal-like shape or a hexagonal shape seen as a planar view, and is a wrench hole to rotate the screw anchor.

FIG. 33 depicts the state where the tooth circumference direction of the in-hole thread 56 is formed to be intermittent, and these examples are described in Patent Document 1 and Patent Document 3. FIG. 34 depicts dual holes 57 each having therein a threaded hole and a non-threaded hole partially overlapping with each other, and the dual holes 57 are described in Patent Document 3 and Patent Document 5.

Any one of the above intends to cause the flexibility to be achieved to enable some degree of variation of the direction of the advancement of the screw anchor during a surgical operation. When the in-hole thread mechanism is introduced in the PEEK resin plate, as depicted in FIG. 33(c), a metal thread insert 58 having a tooth circumference direction intermittent thread formed thereon is fitted to be fixed (See Patent Document 1). This thread insert is thinner than the plate, resulting in that disposition of the intermittent thread is not easy or costs remarkably high.

For hard threads each made of titanium or the like, structurally allowed looseness can be used by the non-tooth portion while a change of engagement to vary the orientation of the screw anchor is not necessarily made smoothly. It is not easy to advance the screw anchor in the desired direction. With the dual hole, when the one hole of the dual hole is inappropriate, the other hole copes with the situation. In the case where the radius locking plate is removed, when the engagement of the metal threads is robust, a large operation power is necessary for releasing the screw-fixation and this aggravates the operator. In any case, the operator is forced to use high-level techniques and high-level skills to achieve the engagement to vary the advancement direction.

SUMMARY OF THE INVENTION

When it is attempted to form the radius locking plate using a resin that has an X-ray transmission property as above, it is desired that the in-hole thread can be formed even without the introduction of the metal thread insert. It is also demanded that the thread does not need to be a circumference direction intermittent screw. There is a need for a locking plate, that has high rigidity and a compact resin layer, that achieves high adaptiveness in an attachment to the radius, and that can reduce the load on a manipulation to vary the advancement direction during the execution of a surgical operation.

The present invention was made in view of the above. An object of the present invention is to provide a locking plate system for treatment of a distal radius fracture, that realizes achievement of advantages due to the fact that the radius locking plate is formed using a resin as an essential item, further enhancement of these advantages, compensation for the disadvantages caused by the use of the resin on the other hand, and, additionally, enhancement of the matching property for the metal screw anchor and the resin plate, that is, not only blocking any falling out of the head portion from the plate through-hole of the screw anchor but also enhancement of the close attachment adjustment action property between the resin plate and the radius.

The present invention is applied to a radius locking system that comprises a radius locking plate to be attached as a bridge between a fractured bone piece and a palmer side of a radius main body at the inside of a body for recovering a position and an orientation of the fractured bone piece produced at a distal radius or in a vicinity thereof and subsequently enhance the bone union of the fractured bone piece and the radius main body, and a screw anchor used therefor.

Referring to FIGS. 1 and 3, the radius locking system is characterized in that a radius locking plate 4 is a flat laminate of intermediate molding materials 7 that each include carbon fibers as reinforcing material and thermoplastic resin as a matrix. A screw anchor 5 is made of hard metal.

A shaft portion 10 of the screw anchor 5 has a principal thread 11 formed thereon to achieve a self-tapping action and the outer circumference of a head portion of the screw anchor 5 has an auxiliary thread 13 tapped thereon to achieve a self-tapping action. The diameter of a through-hole 6 provided in the radius locking plate 4, which allows a radius main body 3 and a fractured bone piece 2 to be threadably fixed to the radius locking plate 4 is oversized relative to the principal thread 11, and is undersized relative to the auxiliary thread 13 in the through-hole 6 in its entirety or in its lower half portion.

As depicted in FIG. 4, intermediate molding materials 7E each reinforced by carbon fibers of a 45°-orientation material or a ±45°-orientation woven cloth are used as upper layers and lower layers, and intermediate molding materials 7A and 7D each reinforced by the carbon fibers of a one-direction material or a 0°/90°-orientation woven cloth are used as intermediate layers.

The through-hole 6 has a cylindrical shape as depicted in FIG. 1(b). As depicted in FIG. 9(e), the through-hole may be oversized relative to the auxiliary thread 13 in its upper half portion and also be undersized relative thereto in its lower half portion.

As depicted in FIGS. 14(b) and 14(c), in the through-hole 6 having the cylindrical shape, a circumferentially continuous thread 38, which has a diameter to be increased by the auxiliary thread 13, is tapped in the through-hole in its entirety or in its lower half portion.

As depicted in FIGS. 16(c) and 16(d), the through-hole 6 has a reverse conical frustum shape at least in its opening 6b. The lower half portion of the opening 6b may have a cylindrical shape and have a diameter to be increased by the auxiliary thread 13. As depicted in FIG. 19(c), the circumferentially continuous thread 38, which has a diameter to be increased by the auxiliary thread 13, may be tapped in the cylindrical lower half portion of the thread 38. As depicted in FIGS. 19(a) and 19(b), the circumferentially continuous thread 38, which has a diameter to be increased by the auxiliary thread, may be tapped in the through-hole in the entirety or in the lower half portion of the thread 38.

As depicted in FIG. 20(b), the lower half portion of the through-hole 6 may have a partially spherical shape. As depicted in FIGS. 15(b) and (c), the enveloping surface of the tooth tips lining on and beneath the auxiliary thread 13 is advantageously formed in a partially spherical shape.

Referring to FIG. 1(b), the enveloping surface of the tooth tips lining on and beneath the auxiliary thread 13 may have a reverse conical frustum shape.

As depicted in FIG. 16(b), a PEEK resin 45 may be coated on the surface of the principal thread 11 of the screw anchor 5.

As depicted in FIGS. 24(a) to 24(c), the thread pitch of the principal thread 11 is set to be larger than the thread pitch of the auxiliary thread 13 of the screw anchor 5 or, as depicted in FIGS. 24(*d*) to 24(*f*), the thread pitch of the principal thread 11 is set to be smaller than the thread pitch of the auxiliary thread 13 of the screw anchor 5.

As depicted in FIG. 10(*c*), a metal wire 17 tracing the contour of the radius locking plate 4 is embedded in the edge portion of this plate.

As depicted in FIGS. 5(*a*) and 5(*b*), an intermediate molding material 7Y is coated to the face on the radius counter-approximal face of the flat laminate of the intermediate molding material 7.

As depicted in FIG. 3(*c*), a non-reinforced resin 23 is advantageously applied to the face on the radius counter-approximal face of the flat laminate of the intermediate molding materials 7. In addition/otherwise, as depicted in FIGS. 3(*b*) and 3(*c*), the non-reinforced resin 23 is applied to the face on the radius approximal face of the radius locking plate 4.

As depicted in FIG. 2(*b*), a number of small protrusions 14 are provided on the face on the radius approximal face of the radius locking plate 4. As depicted in FIG. 5(*a*), to provide the small protrusions, the positions corresponding to the small protrusions of the flat laminate 8 are defined by a layer of a PEEK resin compound 30.

As depicted in FIG. 10(*b*), the lateral cross-sectional shape of the radius locking plate 4 is formed to be a substantially crescent shape.

As depicted in FIG. 12, as to the radius locking plate, bending thereof is provisionally set, and typical plural radius locking plates having different lengths and different widths are lined up as semi-finished products 4Q. As depicted in FIG. 13, a finished product of the radius locking plate is a bending-corrected product that is formed by partially heating the semi-finished product 4Q to adapt the distal point thereof to the teardrop recess of the radius for application.

According to the present invention, a radius locking plate having an X-ray transmission property can be acquired. During a surgical operation executed checking a video image, visual observation of the point to be operated is enabled and an accurate operation is thereby realized. The resin radius locking plate is a flat laminate of intermediate molding materials such as a prepreg sheet, and includes compact layers that each have high rigidity and that each include remarkably few air voids. The resin radius locking plate has a quality that any direct threaded hole processing is executable therefor, and after-the-fact tapping of the thread is enabled by the self-tapping executed by the metal screw anchor.

The diameter of the through-hole is oversized relative to the principal thread formed on the leg portion of the screw anchor, which enables the advancement operation to be executed associated with no load on the insertion of the screw anchor. Further, the diameter of the through-hole is undersized relative to the auxiliary thread tapped on the head portion of the anchor in the through-hole in its entirety or in its lower half portion, which enables the auxiliary thread to advance while executing its self-tapping and achieves the restraint force with desired strength. In the removal process of the radius locking plate, the load on the operator necessary for releasing the screw-fixation of the plate is significantly reduced in view of the engagement is done between the metal thread and the resin thread.

The radius locking plate has a thickness of, for example, 2.5 mm while the resin plate of the flat laminate allows any local deformation even through just a little compared to a hard metal plate such as a titanium plate. The fitting property of the radius locking plate for the radius can be improved during the surgical operation using the advancement operation of the screw anchor even when any unintended gap is formed between the resin radius locking plate and the radius.

Any stretching and shrinking of the surface layer are not obstructed in the bending processing during heating when the intermediate molding material reinforced by the carbon fibers of the 45°-orientation material or the ±45°-orientation woven cloth is used in the upper layers and the lower layers. The radius locking plate finished product is easily acquired that has the high fitting property achieved by the shape correction. The intermediate molding material reinforced by the carbon fibers of the one-direction material or the 0°/90°-orientation woven cloth is used in the intermediate layers constituting the portion in the vicinity of the neutral axis of the bending, and any stretching and any shrinking are thereby unnecessary.

The portions achieving the high tension can therefore be actualized. The after-the-fact shape variation is enabled without degrading any mechanical property of the plate, which allows the radius locking plate to be acquired that has the high degree of freedom of the molding (i.e., the desired bending rigidity and the desired torsional rigidity distribution configuration) that otherwise cannot be acquired with any metal plate.

When the space in the through-hole is formed to have a cylindrical shape, the through-hole is undersized in its entirety relative to the auxiliary thread. The auxiliary thread taps a threaded hole that has a substantially small back clearance by the self-tapping action thereof to the cylindrical wall face. The undersize of the through-hole in its entirety creates the restraint state of the desired strength associated with a significant increase of the torque. The upper half portion of the through-hole may be set to be oversized relative to the auxiliary thread and the lower half of the through-hole may be set to be undersized relative the auxiliary thread. In this case, the restraint force with the desired strength can be achieved gradually increasing the torque by the screw anchor that advances increasing the diameter of the lower half portion.

In the entirety or the lower half portion of through-hole having the cylindrical shape, the circumferentially continuous thread enabling the screw-fixation tapping of the auxiliary thread is formed to be undersized. The screw anchor that advances increasing the diameter of this thread realizes the restraint force resin with the desired strength gradually increasing the torque.

An opening of the space in the through-hole is advantageously formed to have the reverse conical frustum shape. The through-hole in this case also at least partially comprises a portion that is undersized relative to the auxiliary thread tapped on the head portion of the screw anchor. The auxiliary thread taps a threaded hole that has a substantially small back clearance by the self-tapping action whose torque gradually increases against the face having the reverse conical frustum shape.

The partial undersize of the through-hole creates the restraint state of the desired strength reducing the increase of the torque. The self-tapping action of the screw anchor also enables the advancement that is inclined against the axis line of the through-hole having the reverse conical frustum shape. Pulling of the fractured bone piece in a convenient direction and fine adjustment of the orientation of the fractured bone piece are facilitated.

The through-hole having the reverse conical frustum shape may be formed to have a cylindrical shape in its lower half portion. The through-hole is undersized relative to the auxiliary thread, which allows the auxiliary thread to tap the threaded hole that has a substantially small back clearance by the self-tapping action thereof to gradually increase the diameter of the hole-defining wall. The tapping action of the screw anchor can also advance to be inclined against the through-hole, and realizes variation of the axis line of the principal thread to the desired direction. Pulling of the fractured bone piece in a convenient direction and fine adjustment of the orientation of the fractured bone piece are enabled.

When the circumferentially continuous thread is tapped that has a cylindrical shape in the lower half portion of the through-hole and that has a diameter to be increased by the auxiliary thread, the auxiliary thread taps a threaded hole that has a substantially small back clearance by the self-tapping action thereof gradually increasing the diameter of the hole-defining wall because the through-hole is undersized relative to the auxiliary thread. This creates the restraint state of the desired strength reducing the increase of the torque. The tapping action of the screw anchor can also advance to be inclined against the through-hole, and realizes variation of the axis line of the principal thread into the desired direction. Pulling of the fractured bone piece in a convenient direction and fine adjustment of the orientation of the fractured bone piece are enabled.

A form can be employed to have the circumferentially continuous thread enabling the screw-fixation of the auxiliary thread tapped in the entirety of the through-hole of the reverse conical frustum shaped through-hole or the lower half portion thereof. The through-hole is undersized relative to the auxiliary thread, which allows the auxiliary thread to tap the threaded hole having a substantially small back clearance by the self-tapping action thereof that gradually increases the diameter of the hole-defining wall.

This creates the restraint state of the desired strength reducing the increase of the torque. The tapping action of the screw anchor also enables the advancement that is inclined against the through-hole, and realizes variation of the axis line of the principal thread into the desired direction. Pulling of the fractured bone piece in a convenient direction and fine adjustment of the orientation of the fractured bone piece are enabled.

The upper half portion of the space in the through-hole is advantageously formed to have the reverse conical frustum shape and the lower half portion of the space is advantageously formed to have the partially spherical shape. The same effect is achieved as that of the tooth tips provided on the enveloping surface having the reverse conical frustum shape, and the allowable extent of the direction variation can significantly be increased.

When the enveloping surface of the tooth tips lining on and beneath the auxiliary thread is formed to have a partial spherical surface, the tooth tips gradually achieve the self-tapping action to achieve the desired restraint state suppressing any rapid increase of the torque. The advancement inclined against the through-hole is also enabled to allow any variation of the axis line of the principal thread into a desired direction.

When the enveloping surface of the tooth tips lining on and beneath the auxiliary thread is formed to have a reverse conical frustum face, the tooth tips gradually achieve the self-tapping action to achieve the desired restraint state suppressing any rapid increase of the torque. The advancement inclined against the through-hole is also enabled to allow any variation of the axis line of the principal thread into the desired direction.

When the PEEK resin is coated on the surface of the principal thread of the screw anchor, the load of the advancement is reduced and any breakage and any destruction of the cortical bone are alleviated.

When the thread pitch of the principal thread of the screw anchor is set to be larger than the thread pitch of the auxiliary thread, the resin plate can be tightly attached to the radius associated with the advancement of the screw anchor. This is advantageous to facilitate the tight attachment at the point at which the resin plate acting as a bridge is partially floated from the radius.

The thread pitch of the principal thread may be set to be smaller than the thread pitch of the auxiliary thread. In this case, the resin plate can be disengaged from the radius associated with the advancement of the screw anchor. This facilitates isolation at the point at which the resin plate acting as the bridge is attached too tightly to the radius, or the like, and any blood flow disorder of the capillary blood vessels of the periosteum can be caused to tend to be avoided by releasing the compression caused by the tight attachment.

A metal wire tracing the contour of the radius locking plate is embedded in the edge portion of this plate. The metal wire appears in any X-ray image and thus acts as a marker, which enables easy perception of the relative positional relation between the item to be operated and the plate. Further, determination of suitability or unsuitability of the pulling operation of the fractured bone piece is facilitated.

When the intermediate molding material softened in advance is coated to the face on the radius counter-approximal face of the flat laminate of the intermediate molding material, the carbon fiber ends appearing due to the flat stacking are covered and any direct contact with the body can be prevented.

When the non-reinforced resin is applied to the face on the radius counter-approximal face of the flat laminate of the intermediate molding materials, the contact with the flexor tendon becomes soft compared to that of the metal plate and the interference with the flexor tendon is weakened.

When the non-reinforced resin is applied to the face on the radius approximal face of the flat laminate of the intermediate molding materials, the contact with the radius becomes soft compared to that of the metal plate, and dispersion and leveling of the force of the tight attachment on the surface of the radius tend to be facilitated. The vital load on the epidermal layer of the radius is also reduced.

A number of small protrusions are provided on the face on the radius approximal face or ventral surface of the radius locking plate. Any tight attachment of the plate to the radius over the overall face thereof is avoided and any blood flow disorder of the capillary blood vessels of the periosteum can be caused to tend to be avoided.

When a PEEK resin compound layer is used for the points that correspond to the small protrusions of the flat laminate, formation of small recesses and small protrusions is not obstructed because no fiber woven cloth is present. The fiber chips in the compound reinforce the small protrusions and the resin melts to form a recess and protrusion surface layer.

The lateral cross-sectional shape of the radius locking plate is set to be a substantial crescent shape. The center of the lateral cross-section of the radius locking plate can thereby be thickened and the structure can be realized for the rigidity against each of bending and torsion to easily be improved.

The plural typical radius locking plates having different lengths and different widths are lined up by using semi-finished products for which after-the-fact bending variation can be executed. Reduction of the cost can be facilitated because the number of the metal mold types can be suppressed. The radius locking plate is made of thermoplastic resin, which provides a perfectly fitting product corresponding to a custom-made product within a short term when the radius locking plate is bent by after-the-fact deformation.

The radius locking plate can be produced as a bending-corrected product by partial heating, to adapt the distal portion of the semi-finished product to the teardrop recess of the radius to be treated. The radius locking plate is produced to be a perfectly fitting product taking into consideration the individual difference utilizing the property of the thermoplastic resin. Improvement of the fitting property also avoids the possibility that the radius locking plate is displaced toward the proximal portion.

BRIEF DESCRIPTION OF DRAWINGS

FIG. 1 depicts components of a locking plate system for treatment of a distal radius fracture according to the present invention.

FIG. 1(a) is a diagram seen from the palmer side on which a locking plate is attached to a radius to fix a fractured bone piece onto the distal side of the radius.

FIG. 1(b) is a plate partial diagram of an example of a screw anchor and a cylindrical through-hole portion into which the screw anchor is inserted.

FIG. 2(a) is a schematic diagram of a face on the radius approximal face on which a number of small protrusions are provided, FIG. 2(b) is a front elevation diagram, FIG. 2(c) is a front diagram, and FIG. 2(d) is a central longitudinal cross-sectional diagram.

FIG. 3(a) is a cross-sectional diagram of the radius locking plate formed by flatly laminating intermediate molding materials and a resin compound on each other.

FIG. 3(b) is a cross-sectional diagram of the case where a non-reinforced resin is applied to the small protrusions.

FIG. 3(c) is a cross-sectional diagram of the case where the non-reinforced resin is applied to the overall face of the locking plate.

FIG. 3(d) is a cross-sectional diagram of the case where the intermediate molding materials are bent and stacked on each other.

FIG. 4(a) is a diagram of the intermediate molding materials having different fiber orientations.

FIG. 4(b) is a diagram of equal-height face layers assigned to the intermediate molding materials.

FIG. 7(a) is a partial diagram of a one-direction material,

FIG. 7(b) is a partial diagram of a +45°-orientation material cut out from FIG. 7(a), FIG. 7(c) is a partial diagram of a −45°-orientation material cut out from FIG. 7(a), FIG. 7(d) is a partial diagram of a 0°/90°-orientation woven cloth, and FIG. 7(e) is a partial diagram of a ±45°-orientation woven cloth cut out from FIG. 7(d).

FIGS. 9(a) and 9(b) are process step diagrams of insertion matching with the axis line of the hole.

FIGS. 9(c) and 9(d) are process step diagrams of insertion inclined against the axis line of the hole.

FIG. 9(e) is a cross-sectional diagram of the case where the upper half portion is oversized relative to an auxiliary thread and the lower half portion is undersized relative thereto.

FIG. 10(a) is a perspective diagram of the plate whose point to be valley-folded by partial heating is indicated by a chain line for the portion of a semi-finished product corresponding to a distal portion to adapt to a teardrop recess of the radius to be treated.

FIG. 10(b) is a schematic diagram of an example of the case where the lateral cross-sectional shape of the radius locking plate is formed to be a crescent shape.

FIG. 10(c) is a schematic diagram of the radius locking plate whose edge portion has a metal wire tracing the contour of the plate embedded therein.

FIG. 13(a) is a schematic diagram of an example of an apparatus to bend a thick portion.

FIG. 13(b) is an explanatory diagram of deformation of a burr portion.

FIG. 13(c) is a diagram of an example of a burr portion heating apparatus.

FIG. 15(a) is a diagram of a dimensional relation between the screw anchor comprising the auxiliary thread whose enveloping surface of the tooth tips lining on and beneath of the auxiliary thread forms the reverse conical frustum face, and the cylindrical through-hole, and FIGS. 15(b) and 15(c) are cross-sectional diagrams of the case where the enveloping surface of the tooth tips lining on and beneath the auxiliary thread forms a partial spherical face.

FIG. 16(a) is a plan diagram of the radius locking plate.

FIG. 16(b) is a cross-sectional diagram of the screw anchor whose principal thread is coated by a resin.

FIG. 16(c) is a cross-sectional diagram of a portion of the plate at the through-hole point and the screw anchor facing the plate.

FIG. 16(d) is a cross-sectional diagram of the portion of the plate whose lower half portion of the through-hole has a cylindrical shape and the screw anchor facing the plate.

FIG. 19(a) is a partial diagram of the plate whose thread formed on the through-hole has the reverse conical frustum shape in the entirety of the through-hole.

FIG. 19(b) is a partial diagram of the plate whose thread on the lower half portion of the through-hole has the reverse conical frustum shape.

FIG. 19(c) is a partial diagram of the plate whose thread on the lower half portion of the through-hole has a cylindrical shape.

FIG. 19(d) is a partial diagram of the plate whose lower half portion of the through-hole has a partially spherical shape.

FIGS. 23(a) and 23(b) are cross-sectional diagrams of the through-hole whose inner diameter and the valley-bottom diameter after the diameter increase are increased relative to those before the diameter increase.

FIG. 23(c) is a cross-sectional diagram of the through-hole whose valley-bottom diameter is equal but whose inner diameter after the diameter increase is increased relative to that before the diameter increase.

FIG. 31 discloses X-ray images of the state where a metal radius locking plate is clearly perceived and the affected site is thereby hidden.

FIGS. 33(a) and 33(b) are cross-sectional diagrams of an example of a prior art proposal according to which the tooth circumference direction of the thread tapped in the through-hole is intermittent, and FIG. 33(c) is a partial cross-sectional diagram of a resin plate into which a metal screw insert is fitted to be fixed.

FIG. 34 discloses cross-sectional diagrams of an example of a prior art proposal that uses dual holes each having a hole with a thread and a hole with no thread.

EMBODIMENTS OF THE INVENTION

Figure 2:
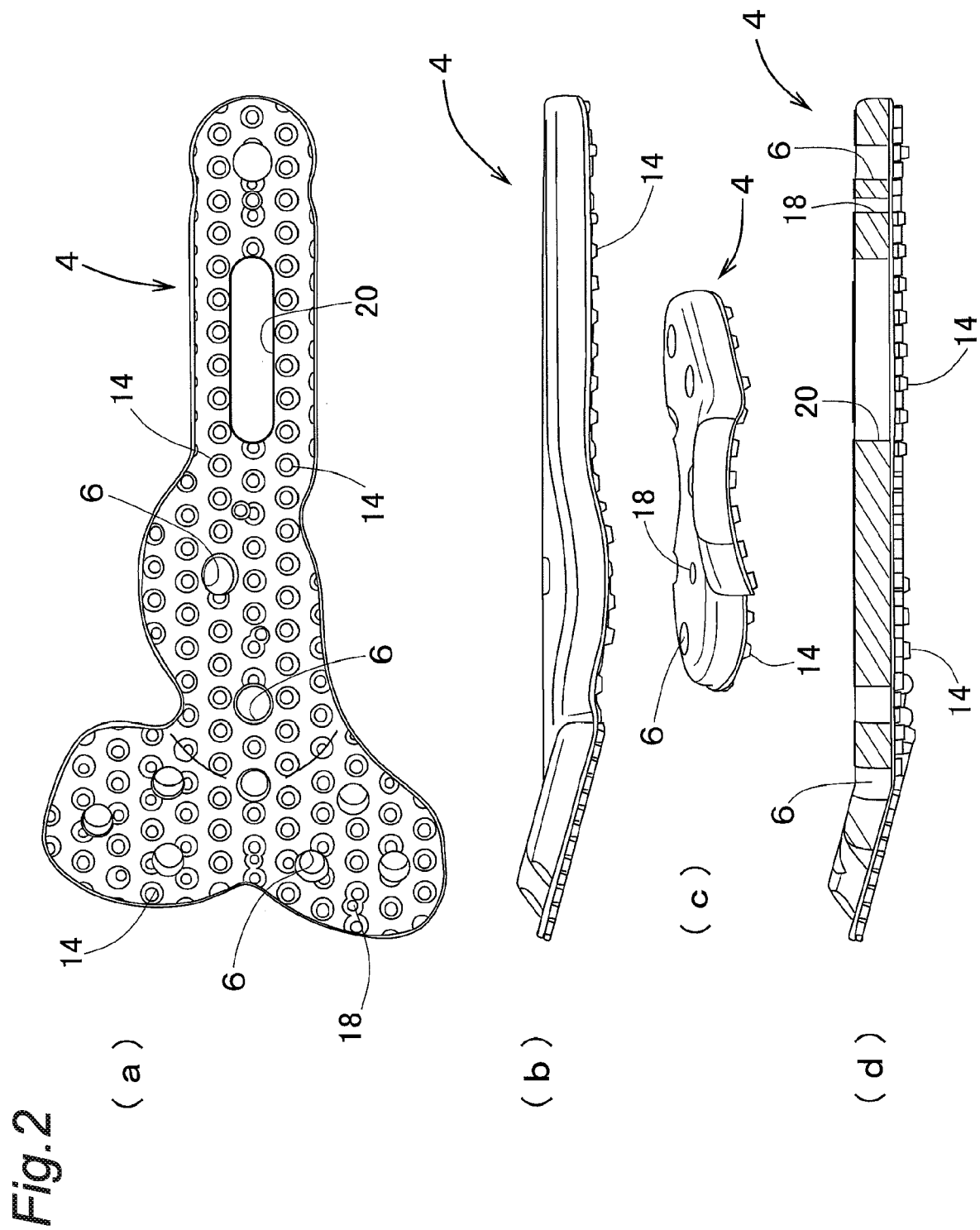
FIG. 2 depicts the radius locking plate.

A locking plate system for treatment of a distal radius fracture according to the present invention will be described below in detail referring to drawings having embodiments thereof depicted therein. The present invention creates the locking plate system for treatment of a distal radius fracture that is a ready-made product but that achieves the compatibility with the radius matching that of a custom-made product, by making excellent use of the detailed analyses of various types of information on the human bone measurement, and the recent body simulation technique.

The system is realized by, for example, facilitating use of a composite material as the raw material of the radius locking plate for the plate to have the structure and the mechanical properties of the rigidity that are suitable for a surgical implement to be implanted in a body for a bone fragility fracture and to improve the shape compatibility. In addition, the present invention attempts to include in the plate a restraint mechanism that utilizes the properties of the composite material product expecting improvement of the precision of the fixation of the radius locking plate to a radius using a screw anchor.

FIG. 1(a) depicts an example of the radius locking plate 4 attached on the palmer side in a body to fix a fractured bone piece 2 of a distal end of a radius 1 to a radius main body 3. FIG. 1(b) depicts an example of the radius locking plate 4 and a screw anchor 5 used therefor. As to the radius locking plate, only the vicinity is depicted of a through-hole 6 having a cylindrical shape into which the screw anchor is inserted. The radius locking plate 4 is attached as a bridge to the fractured bone piece 2 and the radius main body 3 as depicted in FIG. 1(a) to enhance the bone union of the fractured bone piece 2 and the radius main body 3 after recovering the position and the orientation of the fractured bone piece produced at the distal radius or in the vicinity thereof. The screw anchor 5 is a lug screw that advances in the radius 1 through the through-hole 6 that is defined to be suitable for causing the screw anchor 5 to pass through the radius locking plate.

As depicted in FIG. 2(a), the radius locking plate 4 has a number of small protrusions 14 described later provided on the face thereof on the radius approximal face. FIG. 2(b) is a front elevation diagram, FIG. 2(c) is a front diagram, and FIG. 2(d) is a central longitudinal cross-sectional diagram. The radius locking plate 4 is a flat laminate 8 depicted in FIG. 3(a) of an intermediate molding material 7 that includes carbon fibers as reinforcing material and thermoplastic resin as a matrix, and is an article formed by hot pressing forming. Examples of the thermoplastic resin include PEEK (polyetheretherketone) and polyetherimide, and the thermoplastic resin is non-toxic to a human body, is softened by being heated, and is melted by being heated further. This property is significantly different from that of a thermoset resin that is hardened by being heated.

Figure 4:
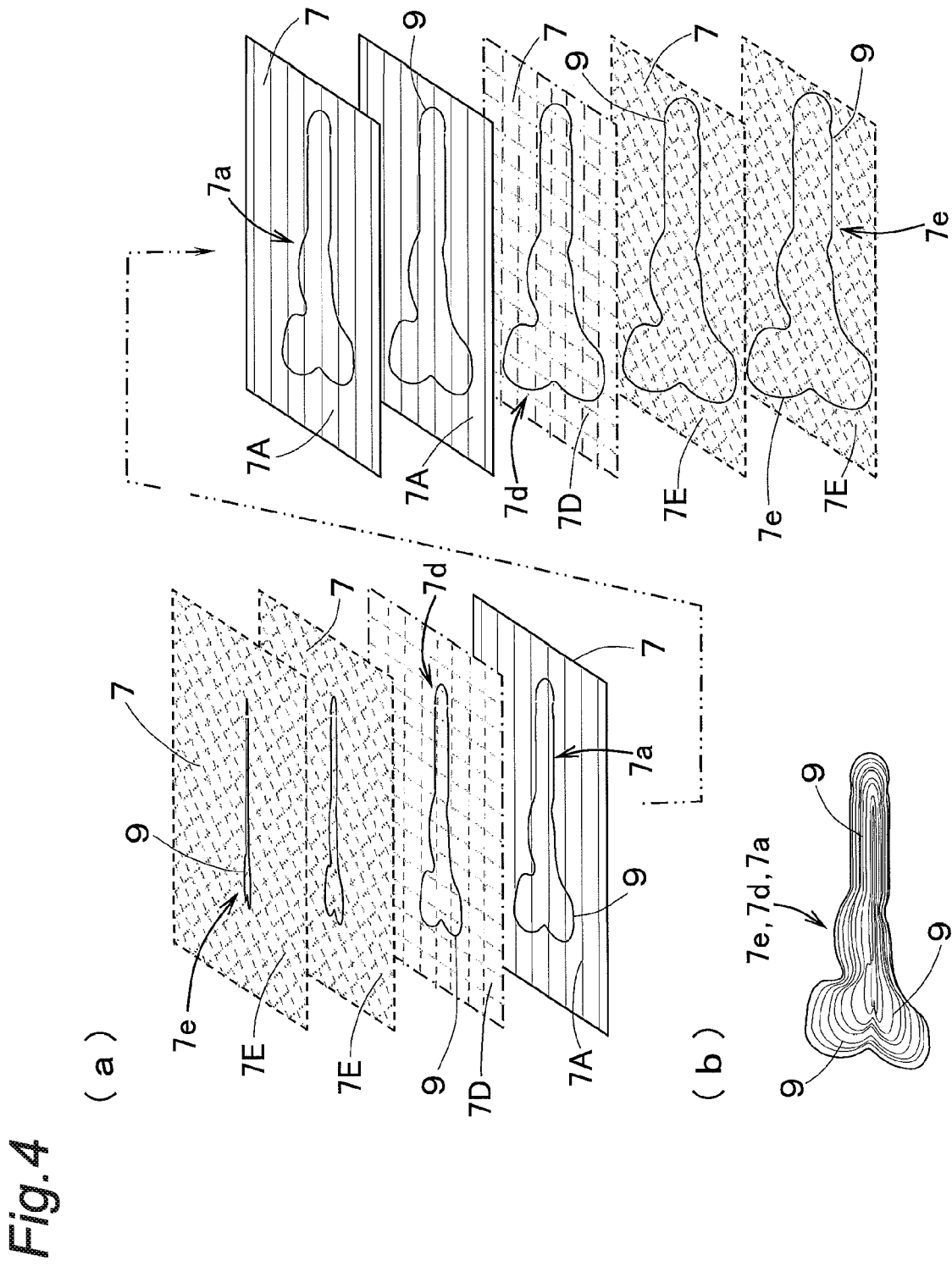
FIG. 4 depicts a graphic explanation of the flatly stacked layers.

The intermediate molding material 7 is a prepreg sheet completely impregnated with the resin or a semi-preg sheet that is a half-impregnated article having a draping property, and incorporates therein carbon fibers as the reinforcing material. These intermediate molding materials are each formed in advance into a plate or a sheet having a thickness of, for example, 0.2 mm and are each cut to have a contour that is a level curve 9 of the radius locking plate 4 as depicted in FIGS. 4(a) and 4(b). These are stacked on each other in a metal mold, are heated and pressured after the mold clamping, and are gradually cooled and the like, and a hardened finished product is acquired.

With reference back to FIG. 1(b), the screw anchor 5 is made of hard, rustproof, and robust metal that typically is titanium or a titanium alloy, and has body safety. A shaft portion 10 thereof has a principal thread 11 formed thereon that has a self-tapping action to advance tapping a thread in the radius 1 by the rotation thereof. A continuous thread 13 (hereinafter, referred to as "auxiliary thread") achieving a self-tapping action is tapped on the circumference of a head portion 12 thereof. To prevent any excessive screwing, shaping the head portion 12 to have the reverse conical frustum shape as depicted is mainly employed at present. The auxiliary thread 13 of the present invention is however not limited to this shape.

The through-hole 6 is oversized relative to the principal thread 11 of the screw anchor 5, and is undersized relative to the auxiliary thread 13 thereof. To be oversized means the hole diameter with which the principal thread 11 can advance therein without any screw-fixation, and no rotation force is necessary for the principal thread 11 to be inserted into the plate. To be undersized means the hole diameter with which the auxiliary thread 13 cannot advance without increasing the hole diameter by self-tapping, and it is required that a rotation force is applied to advance the auxiliary thread 13. Similarly to the feeling of the case of a wood screw, the auxiliary thread gradually creates the restraint state during the advancement of the radius locking plate. Not that all the through-holes provided in the radius locking plate need to be oversized relative to the principal threads of the screw anchors and need to be undersized relative to the auxiliary threads thereof.

Figure 3:
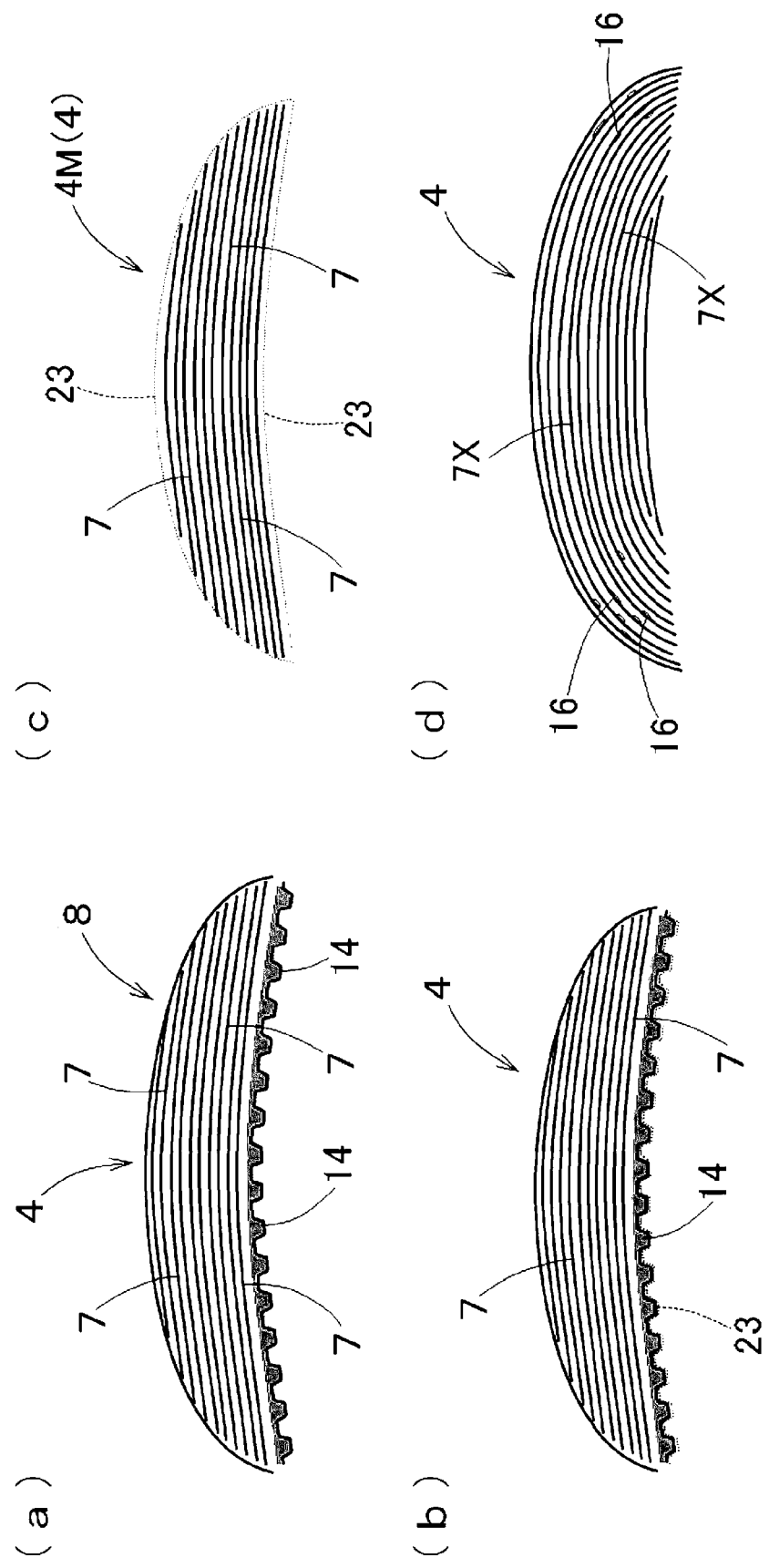
FIG. 3 depicts a portion corresponds to a portion seen from a line between III and III arrows of FIG. 14(a).
Figure 10:
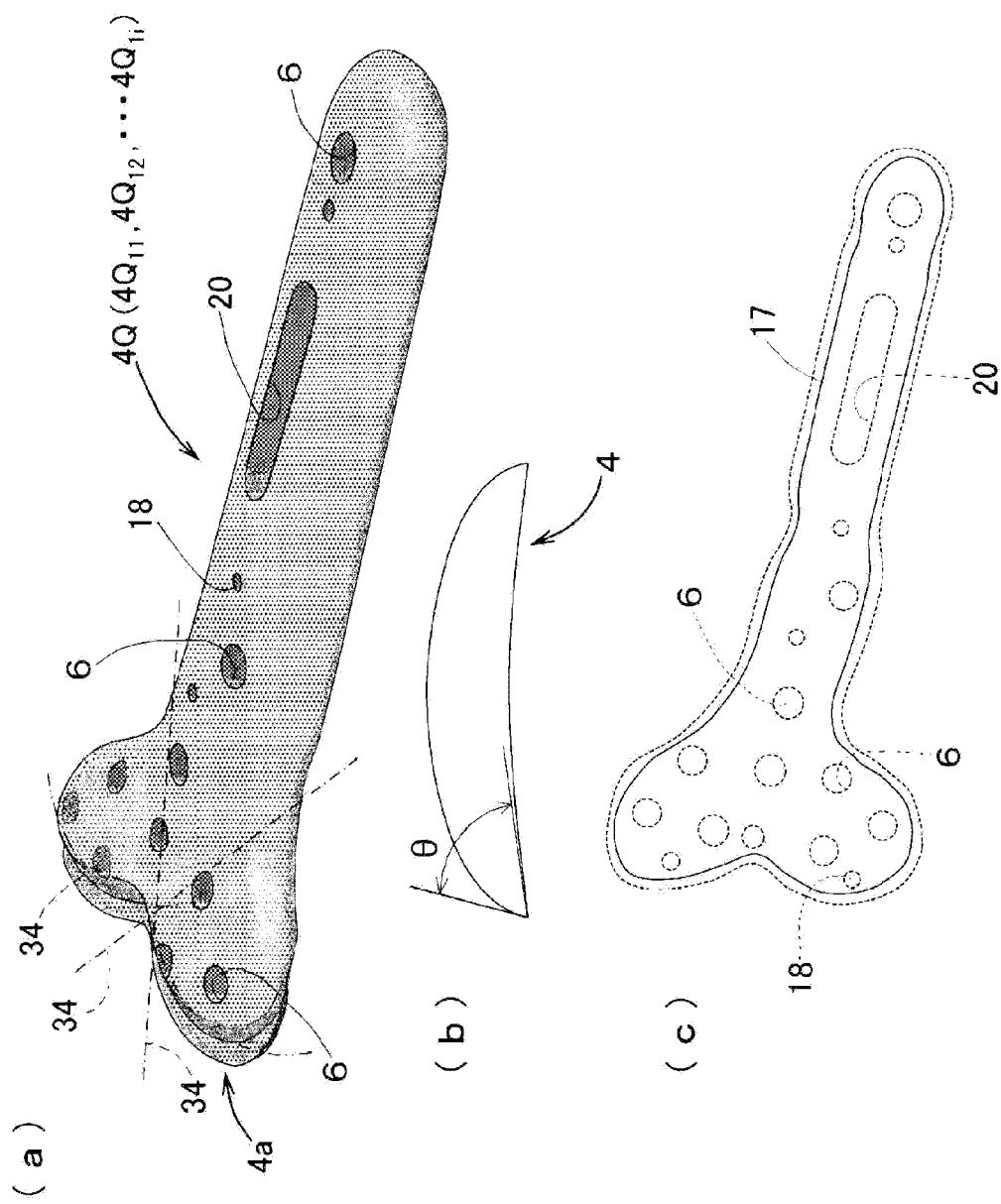
FIG. 10 depicts examples of the radius locking plate.

As depicted in FIG. 3(a) and FIG. 10(b), the resin radius locking plate 4 has the lateral cross-sectional shape that is in principle a substantially crescent shape. To avoid any contact of the radius locking plate with the tendon of the wrist to rupture the tendon, the upper face needs to have smooth shape variation and, in addition, this also is to secure the thickness with which the head portion of the screw anchor can be accommodated. When the central portion in the lateral cross-section of the radius locking plate is thickened, the desired rigidity against each of bending and torsion to be achieved by the plate also tends to be achieved.

The crossing angle θ (see FIG. 10(b)) between the plane on the radius approximal face and the plane on the radius counter-approximal face at the end of the plate is selected to be an angle equal to or smaller than 40° as an indication while the angle θ is determined taking into consideration the proximity with the radius. In any case, occurrence of any flexor tendon failure caused by grazing of the plate that protrudes toward the palmer side with the flexor tendon of the thumb is avoided as much as possible, and gentle contact and compatibility with the tapetum difficult to be achieved by any metal plate can easily be investigated.

As depicted in FIG. 2(b), said a number of small protrusions 14 are provided on the face on the radius approximal face as consideration to soften the contact with the radius, that is, to avoid any blockage against the organic activity of the periosteum. This is based on the intention to avoid any close attachment to the overall face of the radius and, as described later in the section for the procedure for molding the radius locking plate, a PEEK resin compound layer is used for the points corresponding to the small protrusions of the flat laminate.

No woven cloth and no long fiber are present in the compound, enables the disposition of the small recesses and protrusions not to be obstructed. The fiber chips in the compound reinforce the small protrusions and the resin melts to form the recess-and-protrusion surface layer. When the close attachment to the overall face is avoided, any blood flow disorder of the capillary blood vessels of the periosteum is suppressed and this contributes to avoidance of any recrosis of the periosteum.

Though the procedure for molding the radius locking plate will be described later in detail, the overview of the procedure is that the intermediate molding material 7 formed by impregnating carbon fibers with PEEK and hardening these is cut into a predetermined shape of each of the layers, the cut intermediate molding materials 7 are stacked on each other (see FIGS. 4(a) and 4(b)), and fusion between the layers is facilitated using PEEK eluted from the layers during heating. As depicted in FIG. 5(b), an intermediate molding material softened in advance (a softened prepreg sheet) 7Y is advantageously coated on the face on the radius counter-approximal face of the flat laminate 8 (see FIG. 5(a)).

During the increase of the temperature up to about 400° C. thereafter, carbon fiber cut edges 15 exposed at ends of the layers because of the flat laminate can be wrapped up to also be able to avoid any exposure after the molding and hardening. When air cooling is executed after the pressuring, the radius locking plate can be acquired that has a three-dimensionally smooth shape, the robust strength property, the X-ray transmission property, and the body safety. A portion 4a running off the end of the molded article (see FIG. 10(a)) is removed when necessary by a burr removal operation or the like in the finishing processing.

The layers of the flat laminate will be described. As depicted in FIG. 4(a), in each of the portions to be the upper portion layer and the lower portion layer of the radius locking plate, an intermediate molding material 7E is used that is reinforced by carbon fibers of a 45°-orientation material or a depicted ±45°-orientation woven cloth allowing any stretching and shrinking during the softening of the resin.

In the intermediate layer, an intermediate molding material 7A reinforced by carbon fibers of a one-direction material or an intermediate molding material 7D reinforced by carbon fibers of a 0°/90°-orientation woven cloth is used that does not allow any stretching and any shrinking but that achieves a high tension. For example, when nine sheets are used, the sheets are stacked on each other in order of 7E, 7E, 7D, 7A, 7A, 7A, 7D, 7E, and 7E.

Figure 6:
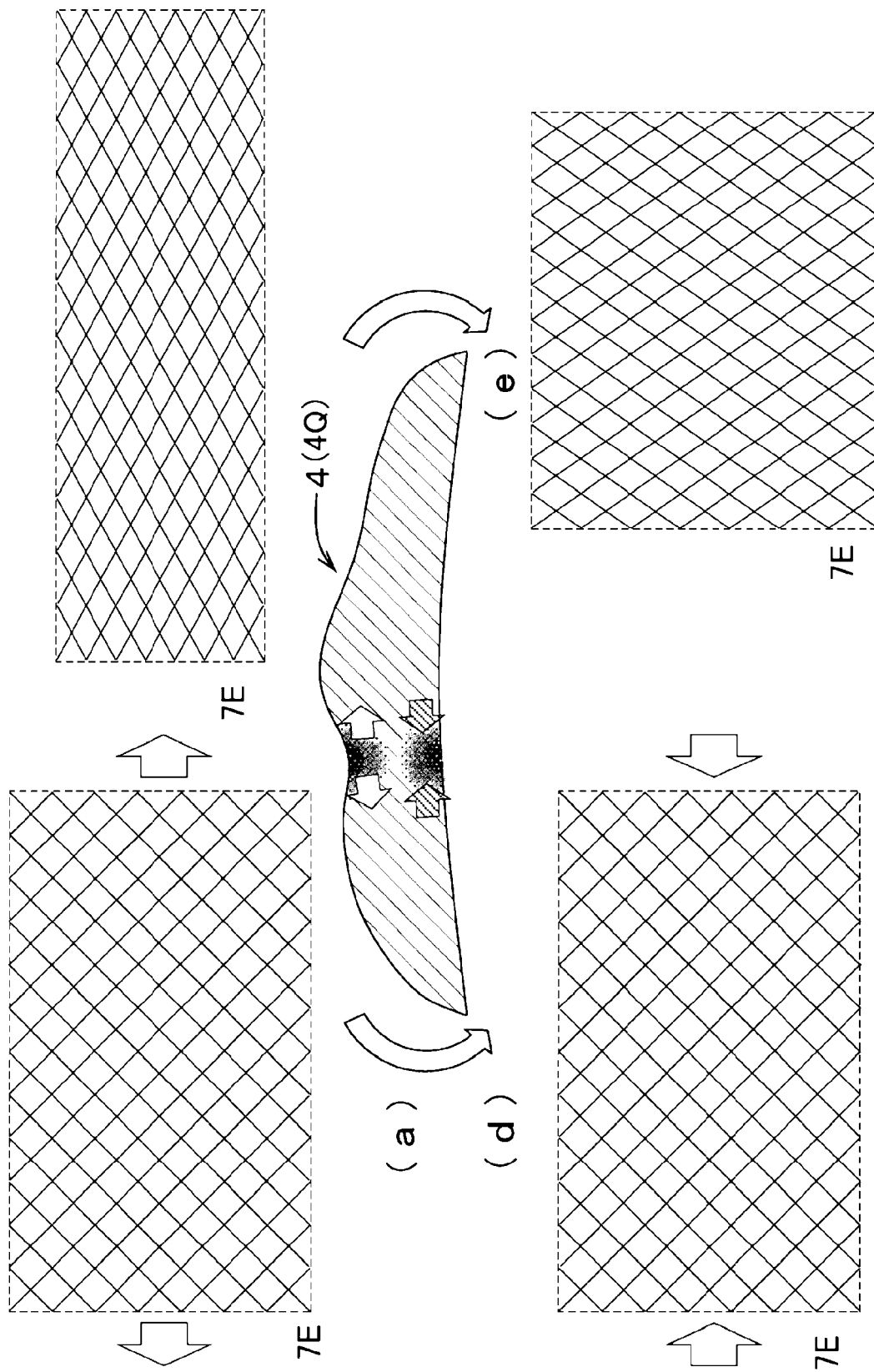
FIG. 6 is a stretching and shrinking behavior diagram of a fiber woven cloth in each of an upper portion layer and a lower portion layer associated with heating and bending of the plate.

When the intermediate molding material reinforced by the carbon fibers of the 45°-orientation material or the ±45°-orientation woven cloth is used in the upper portion layer and the lower portion layer, as depicted later referring to FIG. 13(a), the stretching and the shrinking of the surface layer are not obstructed in the bending processing during heating. As depicted in FIG. 6(a), when a portion of the radius locking plate 4 is somewhat bent downward, the carbon fibers in the upper portion layer stretches in a pantagraph-way from the state of FIG. 6(b) to the state of FIG. 6(c), and the carbon fibers in the lower portion layer shrinks like a pantagraph-way from the state of FIG. 6(d) to the state of FIG. 6(e). The resin of the matrix is molten or semi-molten, which enables any deformation of the carbon fibers not to be obstructed. Even when the resin becomes hardened by cooling, the deformation of the carbon fibers is maintained and the reinforcement effect by the carbon fibers therefore does not vary at all.

The intermediate layer constitutes the vicinity of the neutral face, which eliminates the substantial needs for any stretching and any shrinking of the carbon fibers. The reinforcement by the one-direction material and/or the 0°/90°-orientation woven cloth achieving the high tension is remarkably effective. As above, any after-the-fact shape variation is enabled without degrading the mechanical properties of the radius locking plate, by actualizing the portion achieving the high tension and the portion allowing any stretching and any shrinking. This means that the resin plate has a high degree of freedom of the molding that cannot be achieved by any metal plate.

Figure 7:
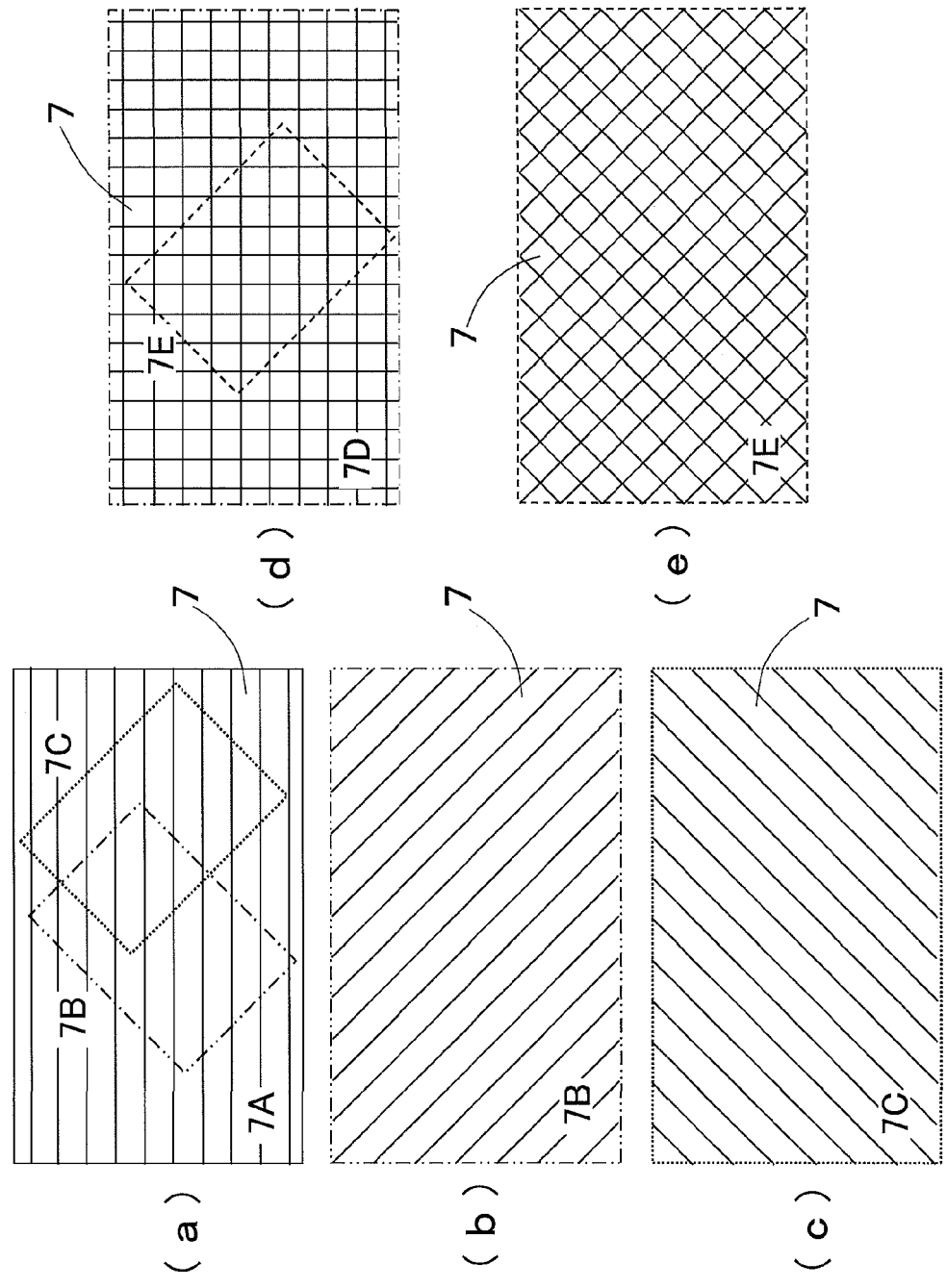
FIG. 7 depicts examples of the orientation of a reinforced fiber in the intermediate molding material.

A radius locking plate can be formed that has the desired bending rigidity and the desired torsional rigidity distribution, by changing the variation of the stacked layers. A radius locking plate finished product can therefore be acquired that has a remarkably high fitting property for the radius by the shape correction. The intermediate molding material 7E depicted in FIG. 7(e) is formed by cutting the intermediate molding material 7D reinforced by the 0°/90°-orientation woven cloth of FIG. 7(d) such that the fiber direction is 45°.

Figure 8:
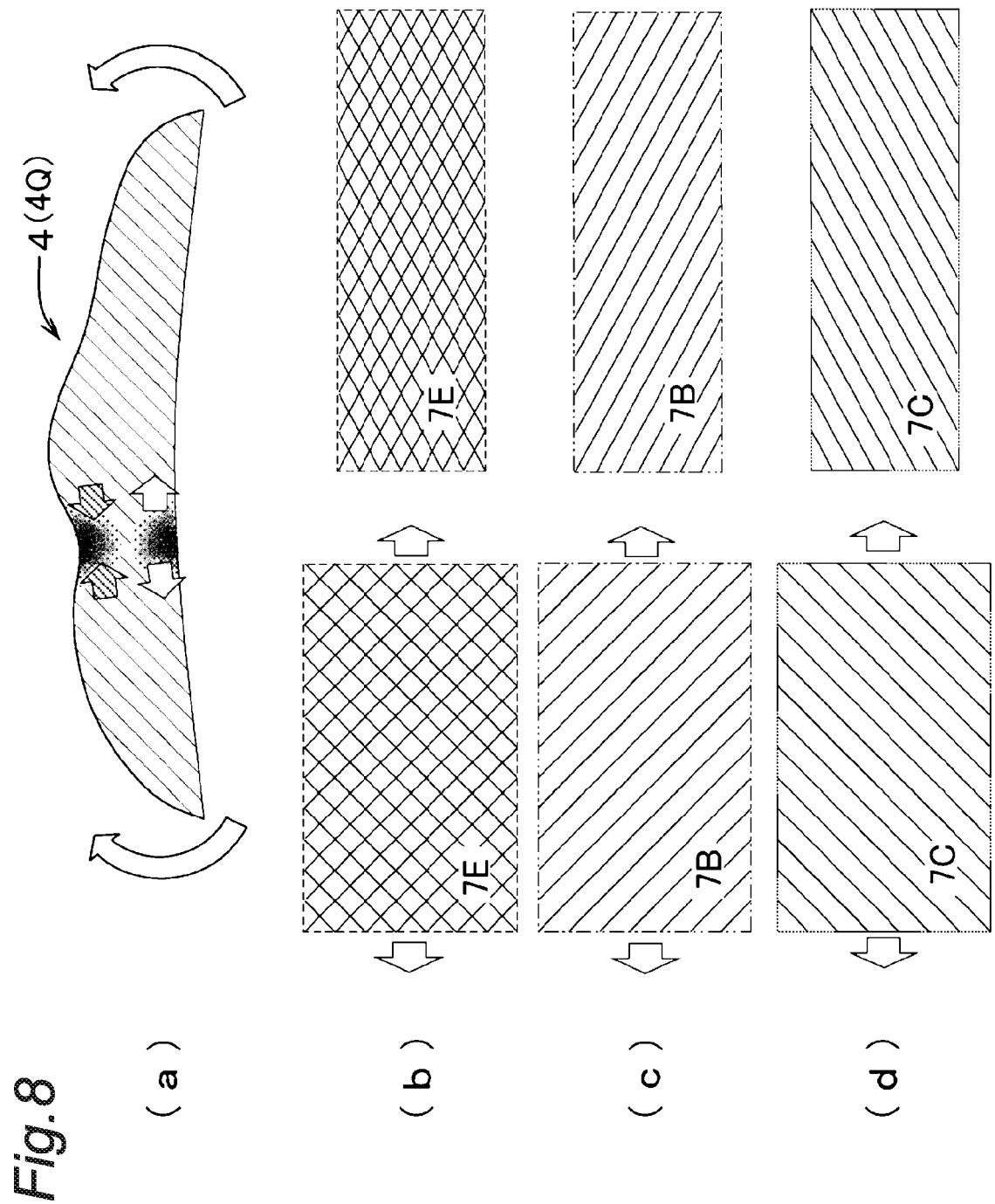
FIG. 8 is an explanatory diagram of stretching of a fiber woven cloth in the lower portion layer associated with the heating and bending of the plate and stretching of the 45°-orientation material stacked in the reverse direction.

The stretching by the pantagraph-like deformation of the carbon fiber woven cloth as depicted in FIG. 8(b) in imparting the bending of FIG. 8(a) to the radius locking plate, has been described referring to FIGS. 6(b) and 6(c). As depicted in FIGS. 8(c) and 8(d), the intermediate molding materials 7B and 7C may be used that are reinforced by the 45°-orientation material and whose orientations are different from each other. These layers are alternately stacked on each other in principle. FIG. 8 depicts the case of the stretching while the case of the shrinking is same. The intermediate molding materials 7B and 7C are formed by only cutting the intermediate molding material 7A reinforced by the one-direction material depicted in FIG. 7(a) such that the fiber orientation becomes +45° or −45°.

The through-hole will be described below. In this example, the through-hole has a simple cylindrical shape. As described referring to FIG. 1(b), the through-hole is oversized relative to the principal thread 11 of the screw anchor 5 and is undersized relative to the auxiliary thread 13 tapped on the head portion thereof. The auxiliary thread advances forming a threaded hole that has a substantially small back clearance by the self-tapping action to the cylinder wall face and therefore creates the restraint state of the desired strength associated with an increase of the torque.

Though it has been described that the reverse conical frustum shape is mainly employed at present for the head portion of the screw anchor 5, in this case, not to mention, the enveloping surface of the tooth tips lining on and beneath the auxiliary thread 13 also forms a reverse conical frustum shape. The tooth tips therefore gradually achieve the self-tapping action and achieve the desired restraint state suppressing any rapid increase of the torque. Any advancement inclined against the through-hole is also enabled and any variation of the axis line of the principal thread to the desired direction is also allowed.

Figure 9:
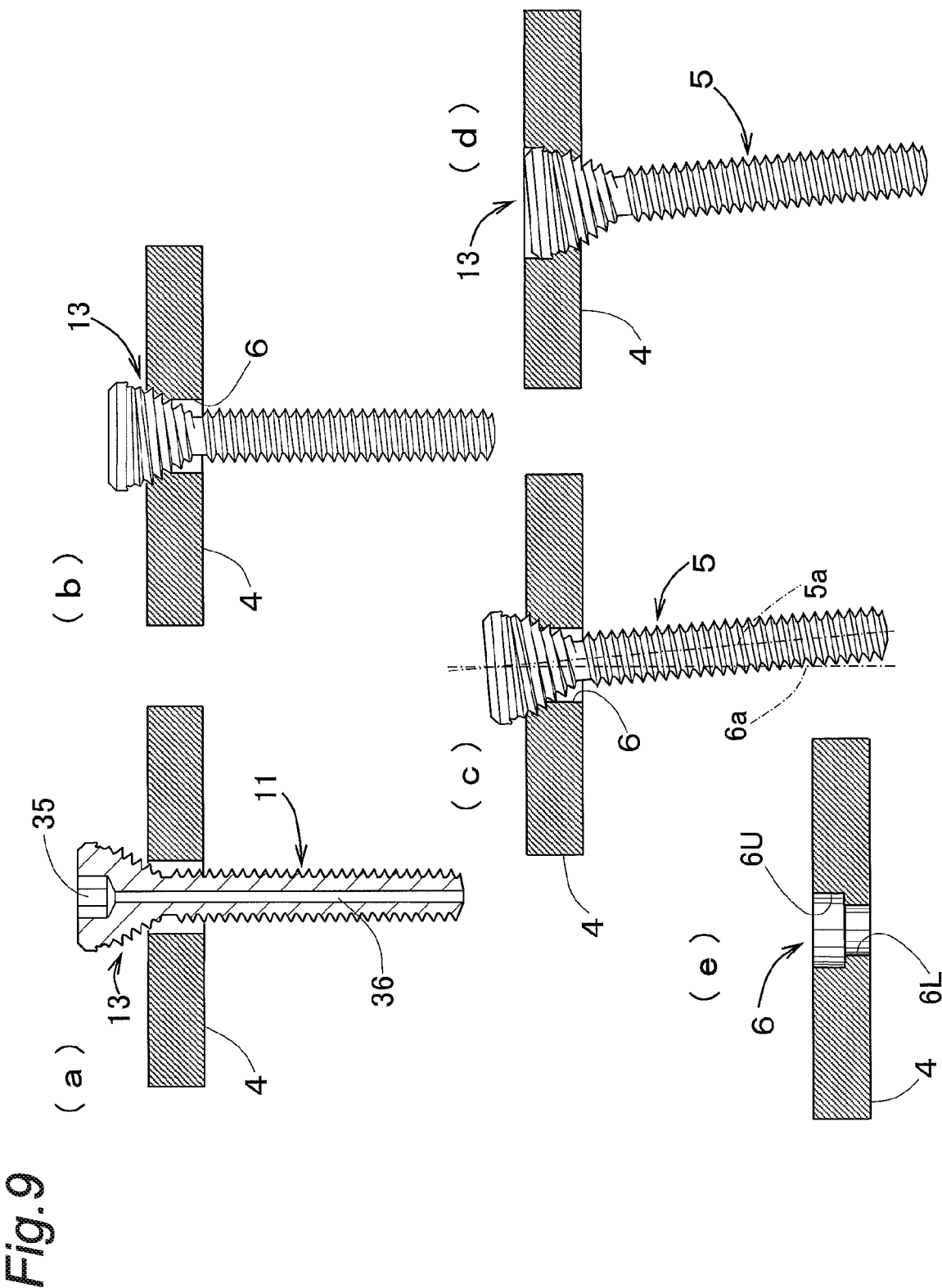
FIG. 9 depicts examples of advancement of the screw anchor of the case where the through-hole is a cylindrical space.

In FIG. 1(b), the thread in a P-zone has no room to screw together with the through-hole 6. During the passage of the thread in the P-zone through the through-hole as depicted in FIG. 9(a), the principal thread 11 of the screw anchor can advance in the radius self-tapping the radius. During the passage of the thread in a Q-zone through the through-hole, the auxiliary thread 13 can gradually self-tap the through-hole 6 as depicted in FIG. 9(b).

The rotation force needs to gradually be increased. The thread cuts into the hole-defining wall while the amount of the produced swarf can be ignored because the extent of crumbling of the resin wall is low. When the thread in an R-zone bites the hole-defining wall, the advancement gradually becomes difficult. The operator is notified of the fact that the screwing reaches its limit. This screwing together also achieves a slacking prevention effect.

As is understood from the above description, according to the locking plate system for treatment of a distal radius fracture, basically, a radius locking plate can be acquired that has the X-ray transmission property in addition to the individual effects described above. During a surgical operation executed based on an image, an accurate surgical operation is realized by enabling the visual observation of the point to be operated that overlaps with the carbon fiber reinforced plastic (CFRP) radius locking plate. The compact layers having high rigidity are acquired in relation to the fact that the flat laminate using the intermediate molding materials is used, and tapping having even quality and high precision as much as possible is therefore enabled, that approximates those of a metal screw anchor.

As to the molding process, the limit residue amount of air voids 16 (see FIG. 3(d)) tends to be cleared because any bent stacked layers of an intermediate molding material 7X (see FIGS. 7(a) to 7(c)) are not used like the one depicted in FIG. 3(d) that closes any escapement for gas bubbles to be pushed out to the edge for degassing. In the removal operation of the radius locking plate executed when the bone union is achieved, the operation force necessary for releasing the screw-fixation is significantly small and the load on the operator is reduced because the fixation is only biting between the metal and the resin.

The radius locking plate has a thickness of, for example, 2.5 mm while the resin radius locking plate of the flat laminate allows local deformation even a little compared to that of a hard metal such as titanium. Even when unintended gap is formed between the radius locking plate and the radius, the fitting property of the radius locking plate for the radius can be improved during the surgical operation by the advancement operation of the screw anchor. This will be exemplified later in detail.

Figure 11:
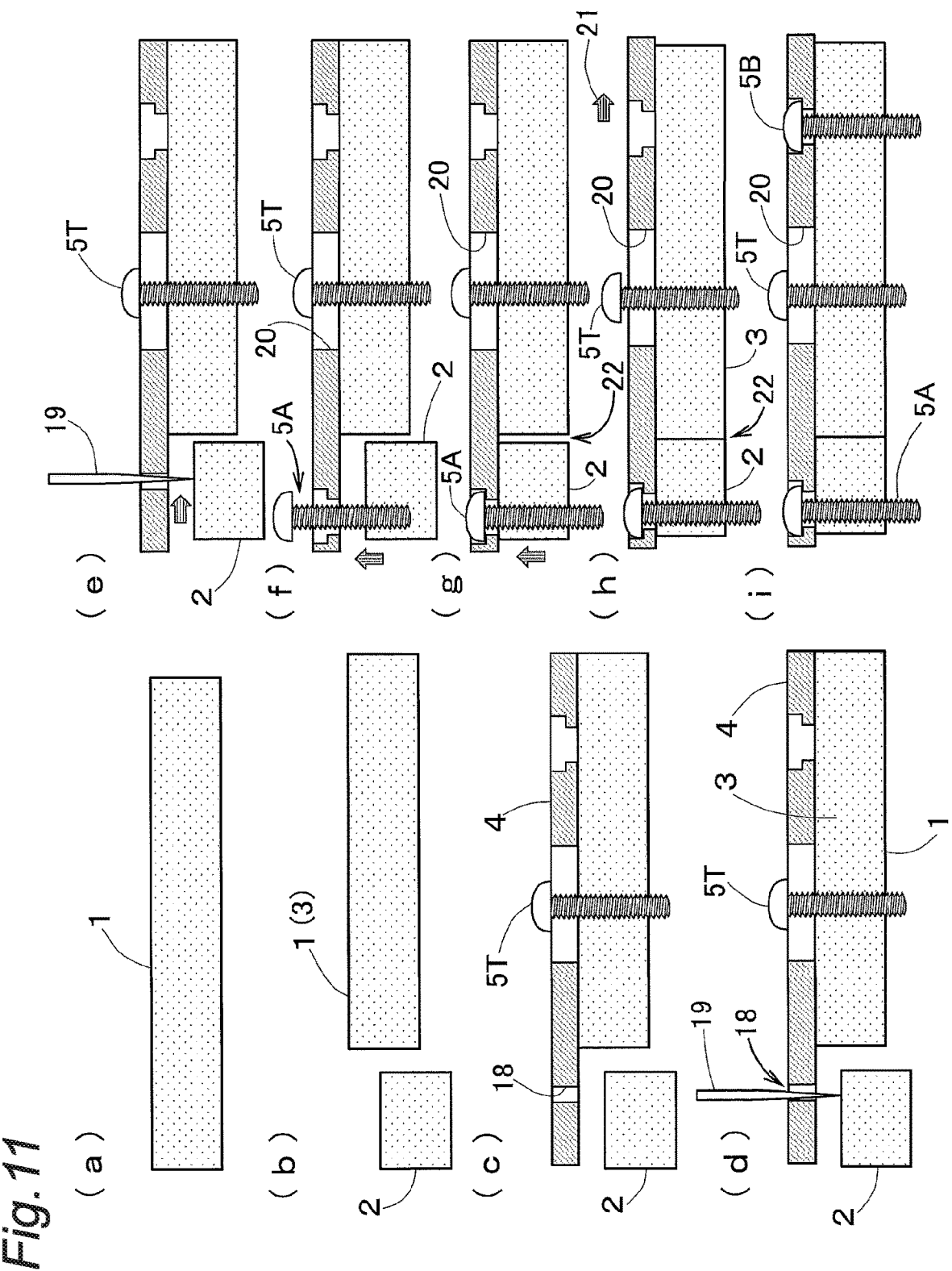
FIG. 11 is a diagram of an example of steps of recovering or correcting the position and the orientation of the fractured bone piece and subsequently placing of a fractured bone piece to be adjacent to a radius main body.

As depicted in FIG. 10(c), a metal wire 17 tracing the contour of the radius locking plate 4 is advantageously embedded in the edge portion of this plate. The metal wire appears in X-ray images and thus acts as a marker, which enables easy perception of the relative positional relation between the item to be operated and the plate, and the degree of the pulling operation of the fractured bone piece 2 can easily be perceived. An example of the operation execution process will be introduced referring to FIG. 11.

FIG. 11(a) depicts the uninjured radius 1 that is simply depicted. FIG. 11(b) depicts the state where the fractured bone piece 2 is produced at the distal end when the radius 1 is injured. In FIG. 11(c), the radius locking plate 4 is attached to the radius 1 on the palmer side and is tentatively fixed by a screw anchor 5T. In FIG. 11(d), a stinger 19 is inserted in one of small holes 18 (see also FIG. 11(a)) provided at a number of points of the radius locking plate 4. In FIG. 11(e), the position and the orientation of the fractured bone piece 2 are recovered or corrected by operating the stinger 19. In FIG. 11(f), a screw anchor 5A is driven into the fractured bone piece 2 to pull up the fractured bone piece 2.

In FIG. 11(g), the fractured bone piece 2 is put adjacent to the radius locking plate 4. In FIG. 11(h), the tentatively fixing screw anchor 5T is somewhat loosened and the radius locking plate 4 is pulled toward the elbow as indicated by an arrow 21 using a long hole 20. In FIG. 11(i), another screw anchor 5B is driven in the state where a gap 22 between the fractured bone piece 2 and the radius main body 3 is narrowed. The tentatively fixing screw anchor 5T is also tightened. When the bone union is achieved as the time elapses in the state where the fractured bone piece is put adjacent to the radius main body, the radius locking plate is removed by releasing the screw anchors by executing the second surgical operation.

As depicted in FIG. 3(b), a non-reinforced resin 23 is advantageously applied to the face on the radius approximal face of the radius locking plate. The contact with the radius becomes soft compared to that of the metal plate, and dispersion and leveling of the force of the tight attachment are facilitated on the surface of the radius. Not to mention, the vital load on the epidermal layer of the radius is also reduced.

Execution of the same treatment for the upper and the lower faces causes no inconvenience even for a radius locking plate 4M having no small protrusion provided thereon as depicted in FIG. 3(c). The non-reinforced resin may be applied instead of the intermediate molding material 7Y (see FIG. 5(b)). Any application session is executed after the molding and the finishing processes are completed.

Figure 12:
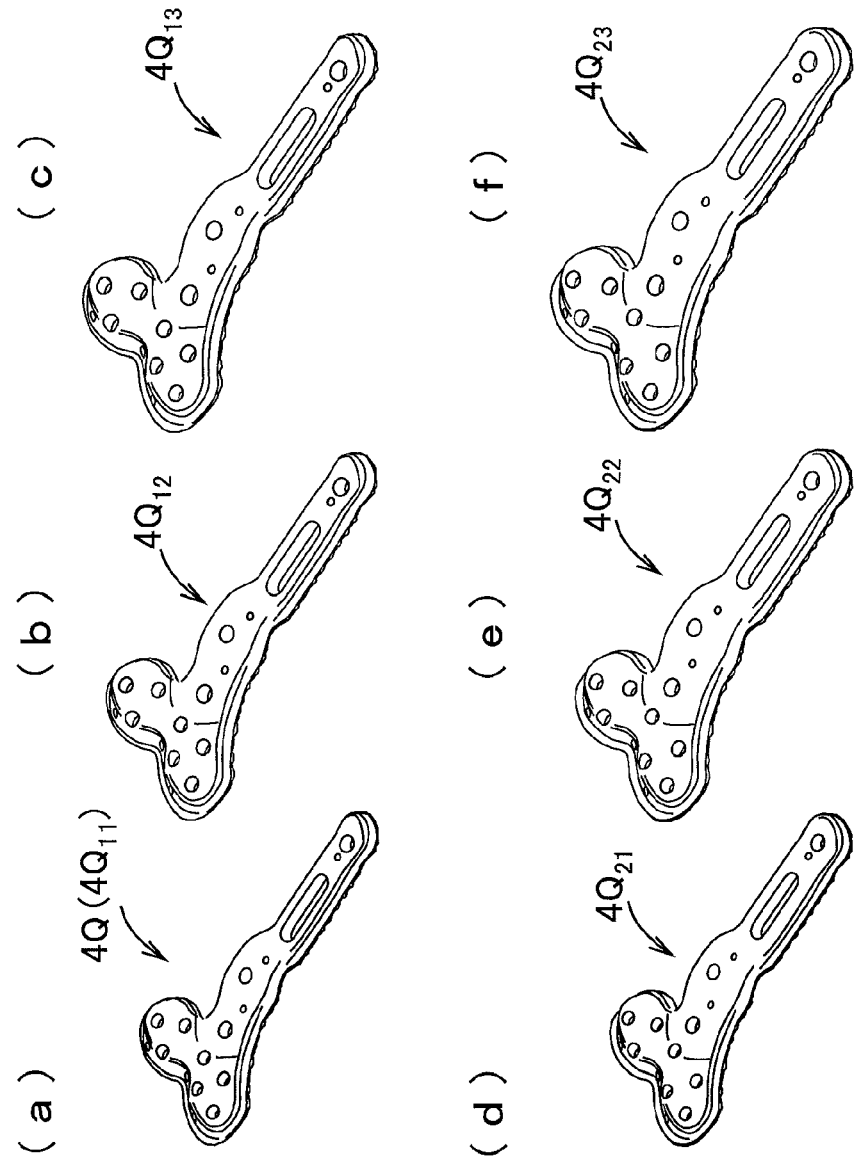
FIG. 12 is a diagram of semi-finished products of the radius locking plate lined up with typical shapes and sizes.

The system comprising the radius locking plate and the screw anchor has been described. Based on these ideas, the radius locking plate is considered to be tentative taking into consideration the bending thereof has room for after-the-fact variation thereof and, as depicted in FIG. 12, typical plural radius locking plates having different lengths and different widths are lined up as semi-finished products 4Q. When the number of lined-up products is large, some of these are usable as they are as finished products.

Figure 13:
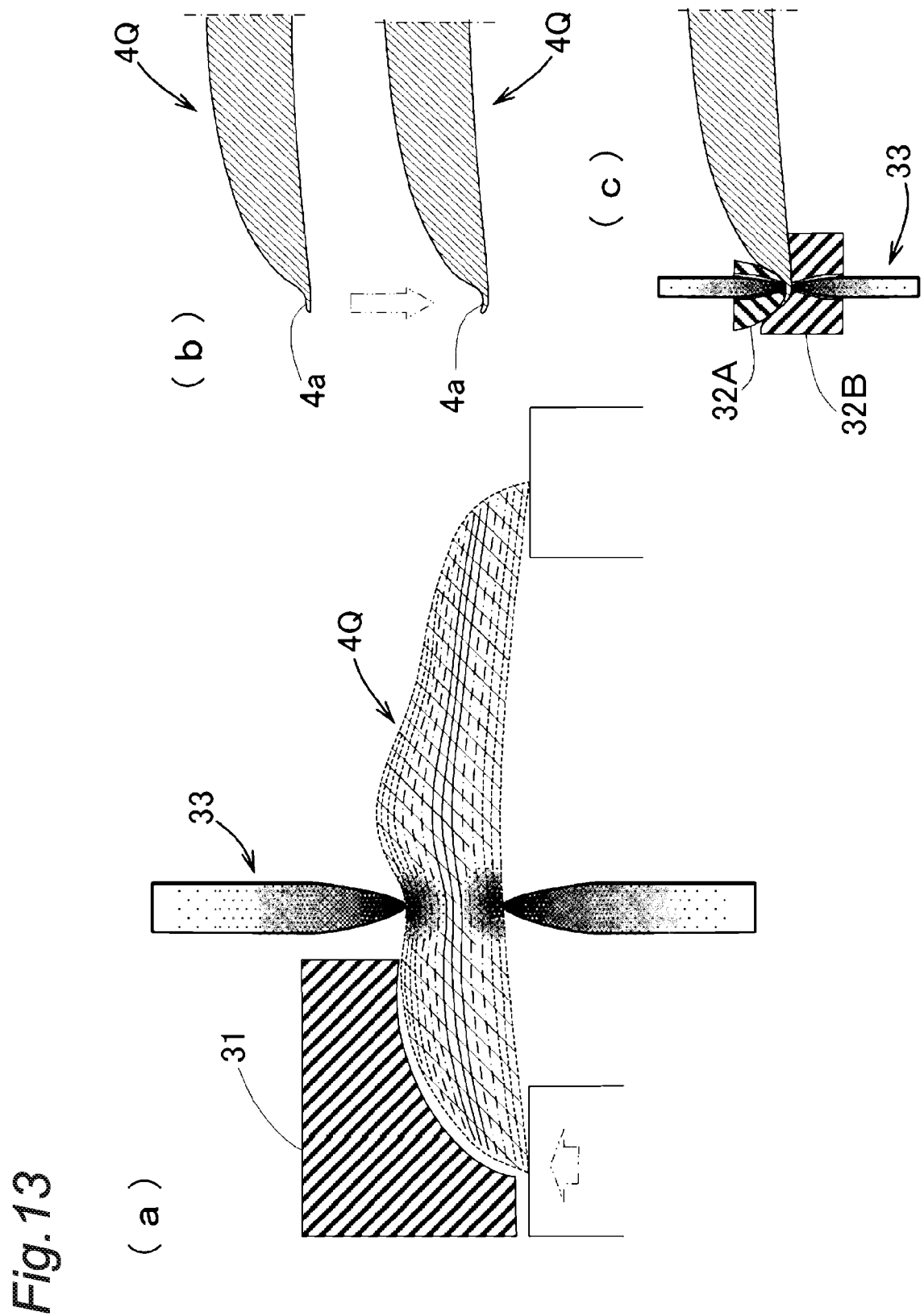
FIG. 13 depicts examples of the state of the heating and the bending of the radius locking plate.

When a bending corrected product partially heated is manufactured according to the procedure of FIG. 13 from the semi-finished products to adapt the distal end portion of the patient for application to the teardrop recess of the radius for application, a finished product of the radius locking plate is acquired. This is a custom-made product that takes into consideration the individual difference by utilizing the properties of the thermoplastic resin.

The possibility is also resolved of shifting toward the proximal portion by slipping caused by bad fitting (insufficient supporting). Worry for any flexor tendon failure is alleviated because consideration is taken to avoid any protruding of the head portion of the screw anchor from the plate toward the palmer side in the vicinity of the teardrop recess.

Figure 5:
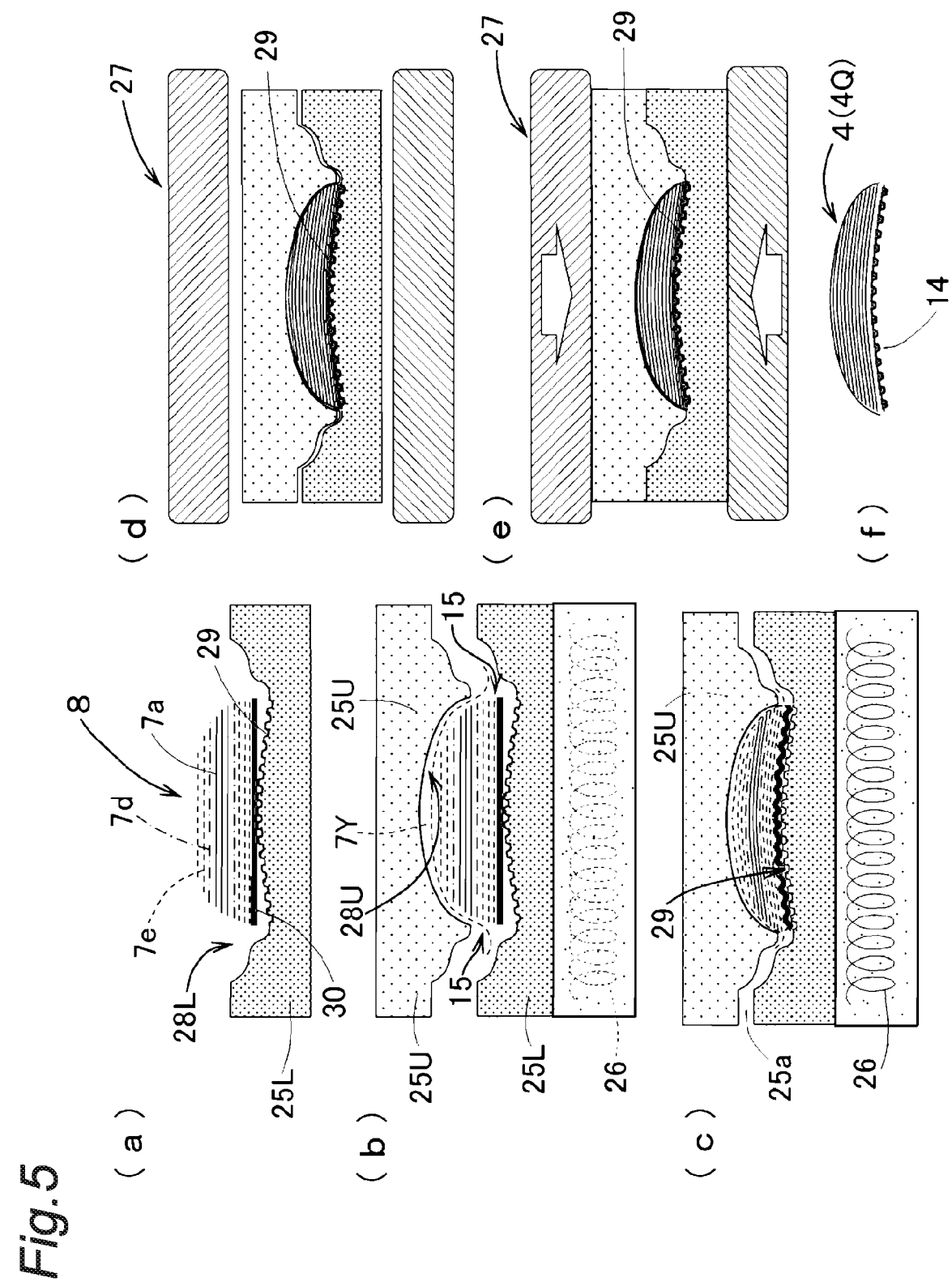
FIG. 5 is a molding process diagram of the resin radius locking plate.

An example of the molding process of the resin radius locking plate 4 will be described referring to FIG. 5. Such items are used as apparatuses as an upper and a lower molding molds 25U and 25L each including a cavity having a shape of the plate, a heater 26 that heats the flat laminate in the molding molds together with the molding molds, and a pressuring machine 27 that pressures the molding molds from above and from beneath. A number of small recesses 29 for providing the small protrusions 14 (see FIG. 3(a)) are provided on the bottom of the cavity 28L to mold the lower half portion of the radius locking plate.

In FIG. 5(a), the PEEK resin compound 30 is placed on the bottom of the cavity. The prepreg pieces 7e, 7d, and 7a (see FIG. 4) are stacked thereon each cut along the level curve. The softened prepreg sheet 7Y depicted in FIG. 5(b) is finally put on the flat laminate 8 to cover the overall flat laminate 8. Though not depicted, guide bars or the like are set up in the cavity when necessary to avoid generation of any horizontal shifting among the layers.

In FIG. 5(b), the upper mold 25U having the cavity 28U provided therein that forms the upper half portion of the radius locking plate is put on. In FIG. 5(c), the compound and the resin of the prepreg pieces are melted by the heater 26 and the volume of the layered body is gradually reduced with, in addition, the weight of the upper mold 25U. The air among the layers at this time is pushed to the ends of the prepreg pieces accompanying the flow of the molten resin, and moves along the inner face of the prepreg sheet 7Y, and degassing is executed in a mating face 25a. In this case, though not depicted, when molding molds are placed under vacuum as necessary, the degassing is more quickly executed.

In FIG. 5(d), the heated molding molds are moved into the pressuring machine 27 and, in FIG. 5(e), a high pressure is instantly applied thereto. The fused article of the prepreg and the compound is hardened during the slow cooling and a block of finished product is formed that has the carbon fibers forming layers therein as depicted in FIG. 5(f). When the finishing process is executed for this, the semi-finished products $4Q_{11}$ to $4Q_{13}$ and $4Q_{21}$ to $4Q_{23}$ of the radius locking plate are acquired that are depicted in FIG. 10(a) or FIG. 12.

The fact that the radius has individual difference has been described and, as depicted in FIG. 12, for the CFRP radius locking plate, the typical plural products having different lengths, different widths, and different bending are prepared as lined-up products, that is, ready-made products. This achieves the purpose of suppressing as much as possible any increase of shapes and types of the molding molds. This is because the bending types are suppressed to tentative one or two based on the lengths and the widths. The process to establish the custom-made plates can be executed only for the case of the resin plates for which the process can be executed after-the-fact, and any molding mold is unnecessary that specially determines the length, the width, and the bending and that is necessary for establishing the custom-made metal radius locking plates.

The case is also present where creation of slight bending is enabled during execution of a surgical operation, and high adaptability can be achieved that cannot be achieved by any metal plate. This is also enabled not by the bent stacked layers each cut along the mold face depicted in FIG. 3(d) but by the flat stacking as depicted in FIG. 3(a). This is because the case is also present where the bending rigidity properly lower than that of the metal plate can be imparted, and this leads to nurturing of operators that each have a high precision fitting technique.

In the present invention, a process utilizing the property of the thermoplastic resin capable of being thermally deformed can be executed for each of the lined-up products. This is because local shaping by partial heating is enabled to adapt the point of the lined-up product corresponding to the distal portion to the recess on the palmer side on the bone distal end of the radius for application.

When the fitting property of the radius locking plate for the radius is degraded, the leveling of the fixation surface pressure by the screw anchor acting on the radius is disrupted. The presence of a low surface pressure indicates the presence of a high surface pressure and causes a further local increase of the load on the radius to also be a factor to delay the recovery.

Necessary are at least the following process steps for the preparation of the semi-finished product and for making it into the finished product. For preparing the semi-finished products of various sizes produced as the ready-made products, X-ray CT photograph data of the radius is summarized and the planar shapes are statistically classified [a first step]. The main parameters are the length and the width, and it is supposed that about four types are assumed for each length and each width to determine, for example, 16 kinds of standard type in total [a second step].

Resin radius locking plates matching with the dimensions and shapes of the standard types are make-to-stock-produced [a third step]. The recovered shape of the radius is computed from the radius X-ray CT data of the patient suffering the fracture, and data on bending is acquired that is suitable for being matched with the teardrop recess of the treated radius. The strict shape and the strict size to be imparted to the radius locking plate are determined [a fourth step].

Shape gauges 31, 32A, and 32B (see the middle section of FIG. 13) of a radius corresponding portion that corresponds to the recovered shape and, when necessary, a hole opening drill guiding tool to form the through-hole for the screw anchor are produced using a three-dimensional printing technique [a fifth step]. The semi-finished product 4Q is locally heated by a heating and deforming apparatus 33 to be plastic-deformable and is processed by bending according to the shape gauges [a sixth step]. A pilot hole is formed in the radius using the hole opening drill guiding tool and the radius locking plate is fixed to the radius using the screw anchor [a seventh step].

To suppress the number of types of the semi-finished products, the tentative number of bend patterns to be the factor to be taken into consideration with the top priority for the fitting is limited to, for example, only one or two for the typical bend pattern(s). The shape of the radius of the patient is also measured and the semi-finished product best approximating this shape is selected. The best adapted product is created by modifying the bending to be matched with the shape of the teardrop recess, and an outstandingly inexpensive custom-made product is thereby produced.

This is because of realization of reduction of the cost of the bend modifying apparatus itself, and simplification of and reduction of the necessary time period for the modification operation. The radius locking plate substantially perfectly fitting the radius achieves a remarkably excellent treatment effect.

The finished product formed by correcting the radius locking plate is created by valley-folding or mountain-folding along any one of chain lines 34 of FIG. 10(a). This is because the distal end of the radius locking plate is the most delicate point in the fitting thereof to the distal radius. As depicted in FIGS. 13(a) and 13(c), insufficient fitting can often be avoided by applying slight after-the-fact deformation. Though the degree of the deformation is low, compared to the metal plate not capable of being deformed, improvement of the positional relations with the navicular bone and the lunar bone present in the vicinity thereof and improvement of the compatibility with the muscle and the tendon present between the plate and these bones are facilitated and the physical load on the patient is therefore significantly reduced.

To the portion 4a running off the end (See FIG. 10(a)), the process of FIG. 13(c) is also applied when intended deformation as depicted in FIG. 13(b) is necessary to contribute to the fitting. These items cannot be considered with any metal radius locking plate. It is assumed that the metal radius locking plate can even be bent, any after-the-fact bending distorts the shapes of the through-holes and the threads, and these holes and threads cannot screw together with any metal screw anchor. The resin plate presents flexible behaviors with respect to the compatibleness of the through-holes and the hole-defining walls with the screw anchors by the advancement of the screw anchors.

The advancement executed when the auxiliary thread of the screw anchor advances straight in the through-hole has been described. Referring to FIGS. 9(c) and 9(d), it can be seen that advancement can be executed with an axis line 5a of the screw anchor 5 not matching with the axis line 6a of the through-hole 6. The advancement can be executed with the axis line of the screw anchor inclined against the axis line of the through-hole. As above, it can be stated that the thread teeth forming the reverse conical frustum enveloping surface have a wide range of options for the advancement direction.

This is often employed when the confidence of the fixation of the radius locking plate to the radius is improved by causing the advancement directions of the plural screw anchors to differ from each other. This is exactly because the screw anchors are made of the hard metal and the radius locking plates are each fully made of the resin. The screwing of the screw anchor is executed through a wrench hole 35 depicted in FIG. 9(a). An example including a cannula 36 of a long hole along the axis line is depicted, but this has no relation with the present invention and will not be described.

The through-hole is undersized relative to the auxiliary thread tapped on the head portion of the screw anchor, which allows the tooth tips provided on the reverse conical frustum enveloping surface to gradually achieve the self-tapping action. This in turn creates the desired restraint state while suppressing any rapid increase of the torque. As above, the self-tapping action of the screw anchor also enables the advancement inclined against the through-hole and realizes the variation of the axis line of the principal thread to the desired direction. This also enables pulling of the fractured bone piece in the convenient direction and the fine adjustment of the orientation of the fractured bone piece.

With the thread formed in the through-hole of a metal plate, the circumference direction needs to be intermittent (see FIG. 33) or a dual hole including a threaded hole and a hole without any thread needs to be employed (see FIG. 34) to enable flexibility of the advancement direction while, with the resin plate, any preparation is unnecessary for allowing the inclined advancement. This is also an advantage of employing the reverse conical frustum shape for the auxiliary thread.

As depicted in FIG. 9(e), the cylindrical through-hole 6 is oversized in its upper half portion 6U and is undersized in its lower half portion 6L relative to the auxiliary thread. In this case, the screw anchor that advances increasing the diameter of the lower half portion can achieve the restraint force of the desired strength gradually increasing the torque.

Figure 14:
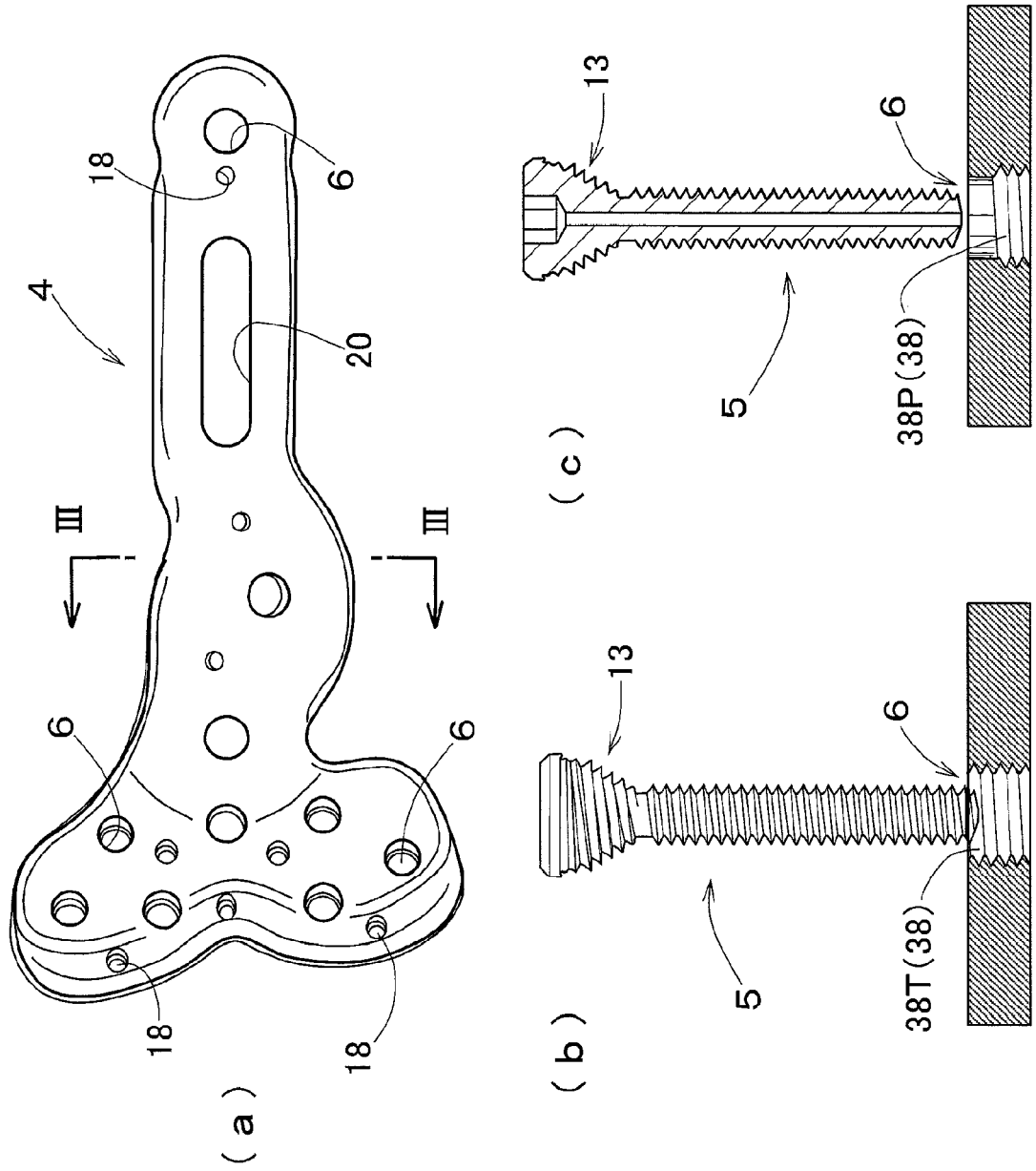
FIG. 14(a) is a plan diagram of an example of the radius locking plate that comprises through-holes whose openings each have a reverse conical frustum shape.
FIG. 14(b) is a partial diagram of the plate on which a circumferentially continuous thread that has a diameter to be increased by the auxiliary thread is tapped on the entirety of the cylindrical through-hole, and an outer appearance of the screw anchor facing the plate.
FIG. 14(c) is a partial diagram of the plate on which the circumferentially continuous thread that has a diameter to be increased by the auxiliary thread is tapped on the lower half portion of the cylindrical through-hole and a cross-sectional diagram of the screw anchor facing the plate.

As depicted in FIGS. 14(b) and 14(c), for the cylindrical through-hole 6, a circumferentially continuous thread 38 that has a diameter to be increased by the auxiliary thread can be tapped on the overall inner face or the lower half portion thereof. This forms an entirely extending thread 38T on and beneath the through-hole 6 or forms a partially extending thread 38P while, in any case, the circumference direction intermittent thread (see FIG. 33) is unnecessary.

With the continuous thread that is easily tapped, the screw anchor advances using the self-tapping only to increase the pitch circle without varying the thread pitch. The rapid increase of the torque in this case is suppressed relative to that of the case of the cylindrical through-hole and, in spite of this, the restraint state of the desired strength is created.

Any metal screw insert (see FIG. 33(c)) does not need to be introduced to introduce the thread mechanism into the resin plate.

Figure 15:
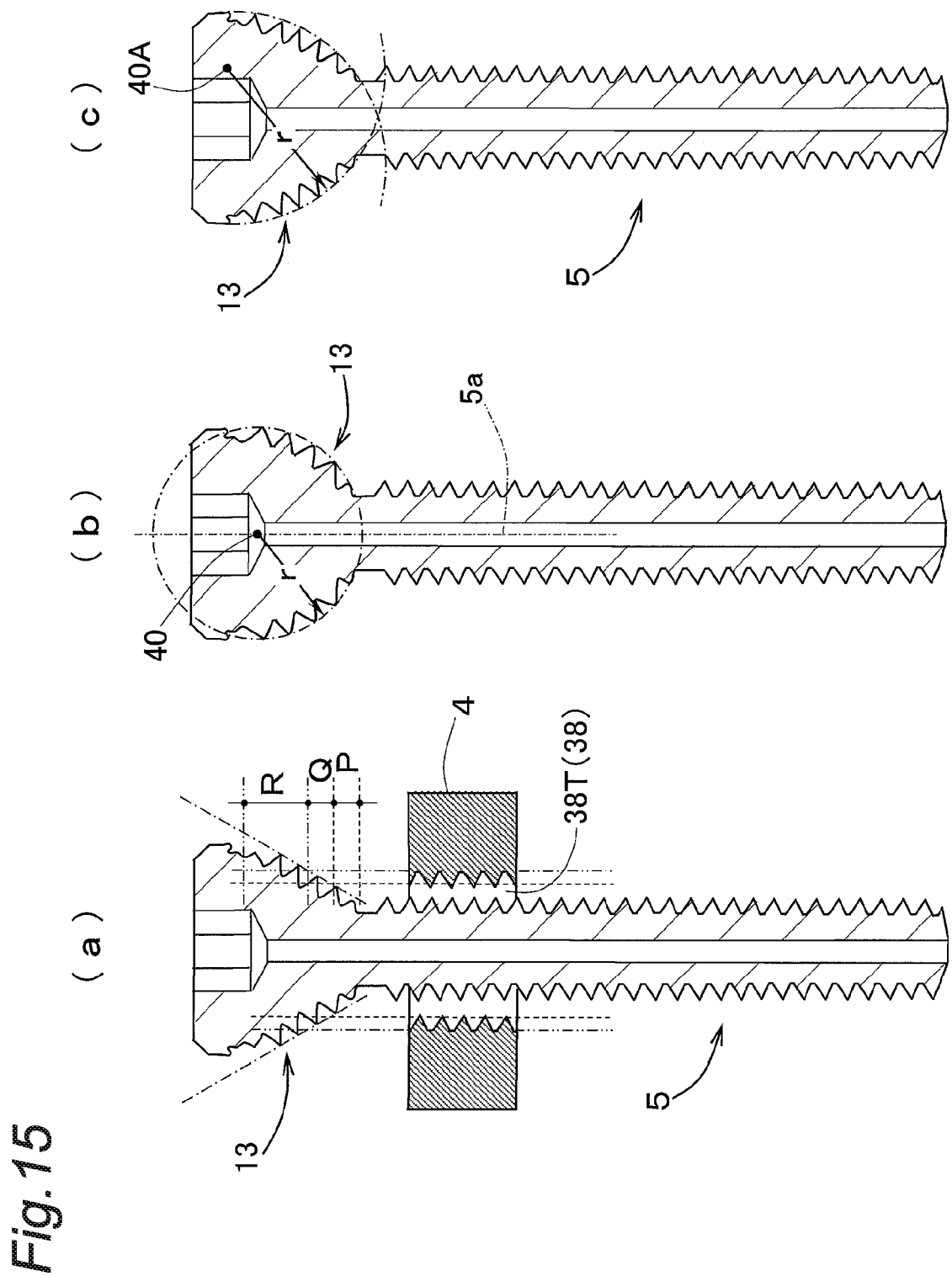
FIG. 15 depicts examples of the shape of the screw anchor.

The behavior in each zone corresponding to FIG. 1(b) in the case where the entirely extending thread 38T is employed can easily be estimated from FIG. 15(a). During the passage of the thread in the Q-zone through the entirely extending thread 38T, though not depicted, the auxiliary thread 13 advances through the entirely extending thread 38T. The auxiliary thread 13 self-taps the entirely extending thread 38T to increase the diameter thereof. The rotation force is gradually increased while the load thereof is smaller than that in the Q-zone of FIG. 1(b).

When the thread in the R-zone bites the hole-defining wall, the advancement gradually becomes difficult and this notifies the operator of the fact that the screwing reaches its limit. The same is applied to the case where the advancement is executed in the partially extending thread 38P. In any case, the self-tapping produces no or a substantially small amount of swarf, and improvement of the screw-fixation strength, and strengthening and densification of the circumference of the through-hole by compressing the threaded hole-defining wall of the through-hole are facilitated.

Figure 16:
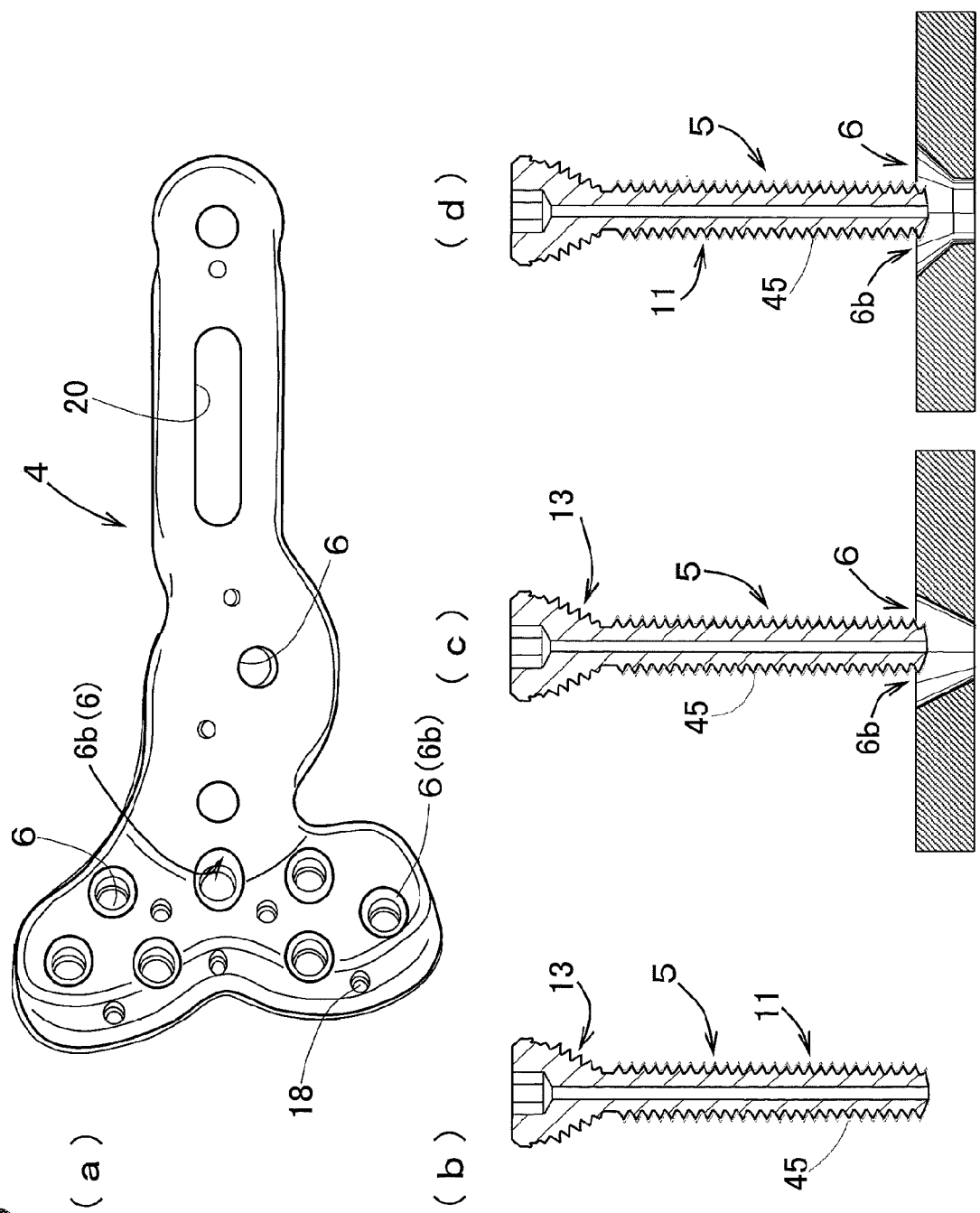
FIG. 16 depicts the state where the whole or a portion of the through-hole forms the reverse conical frustum shape.
Figure 17:
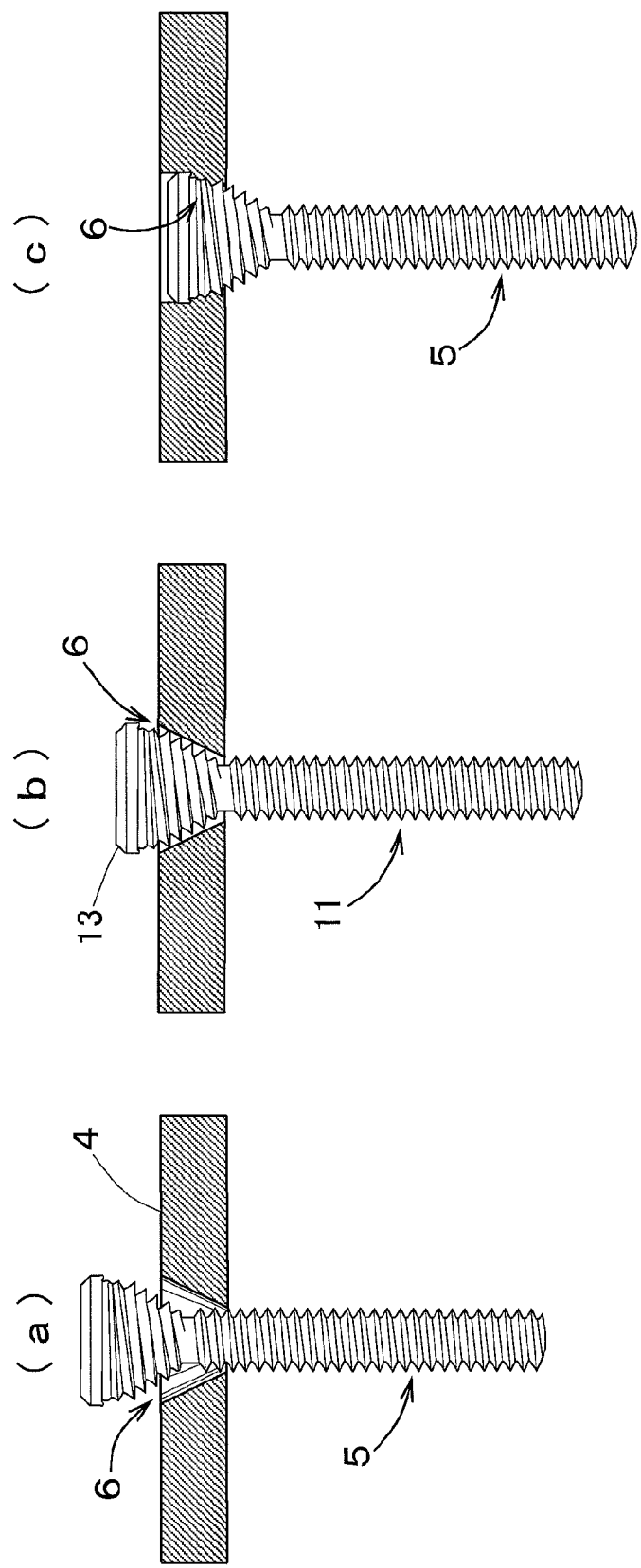
FIG. 17 is a process diagram of advancement of the screw anchor inserted matching with the axis line of the hole when the through-hole has the reverse conical frustum shape.
Figure 18:
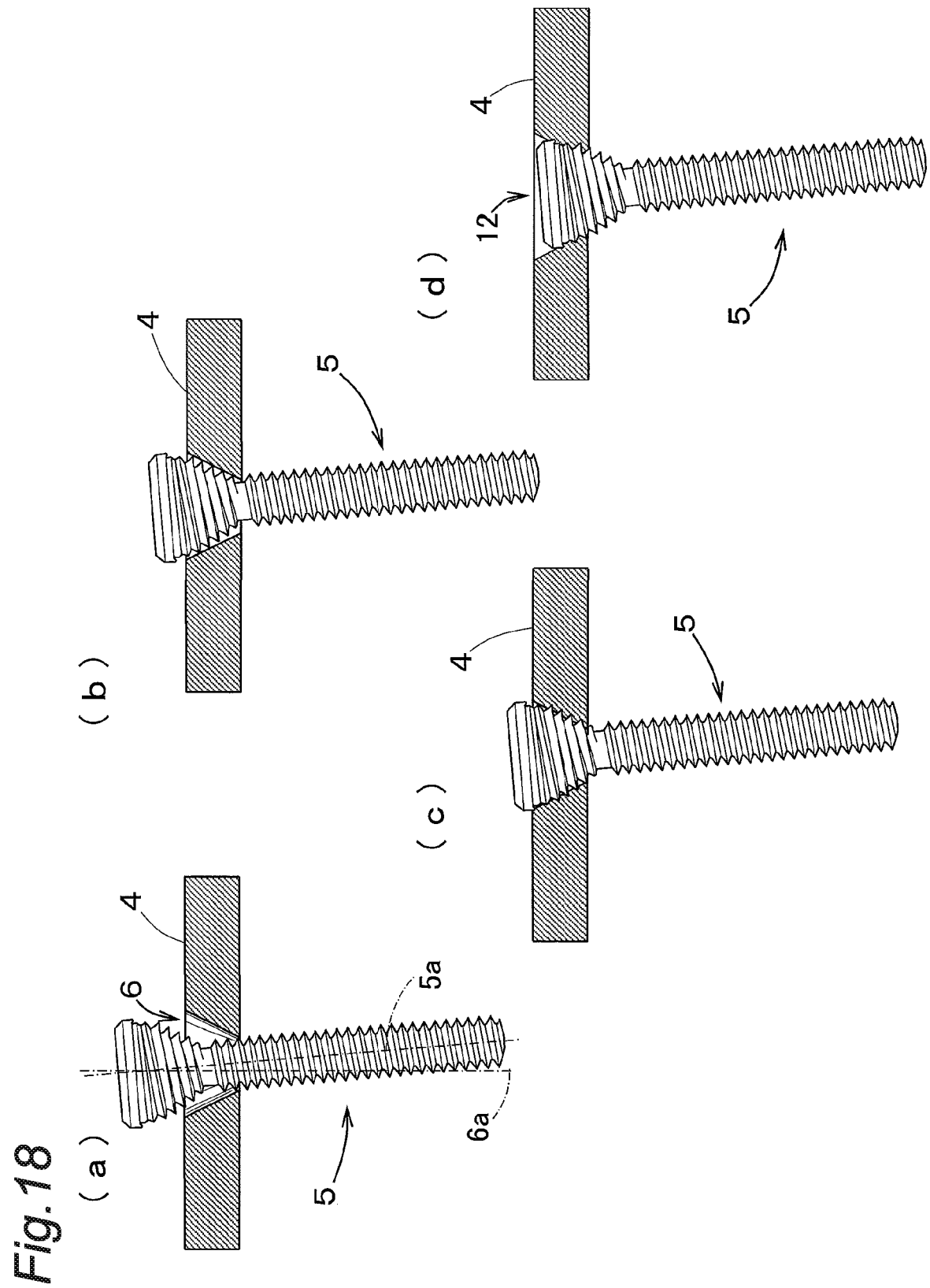
FIG. 18 is a process diagram of the advancement of the screw anchor inserted inclined against the axis line of the hole when the through-hole has the reverse conical frustum shape.

Instead of employing the cylindrical shape for the through-hole 6, as depicted in FIG. 16(c), the through-hole 6 can be formed to have a reverse conical frustum shape in at least its opening 6b. As can be seen from FIG. 16(a), the diameter of the through-hole 6 seen from the palmer side is larger than that of the case of FIG. 14(a) and is often applied to the distal end of the radius locking plate 4. FIG. 17 depicts the state where the screw anchor 5 advances in the through-hole 6 of the radius locking plate by the self-tapping that matches with the axis line of the hole, and is screw-fixed. FIG. 18 depicts the course of the screw-fixation of the screw anchor that advances being inclined against the axis line of the hole.

Figure 19:
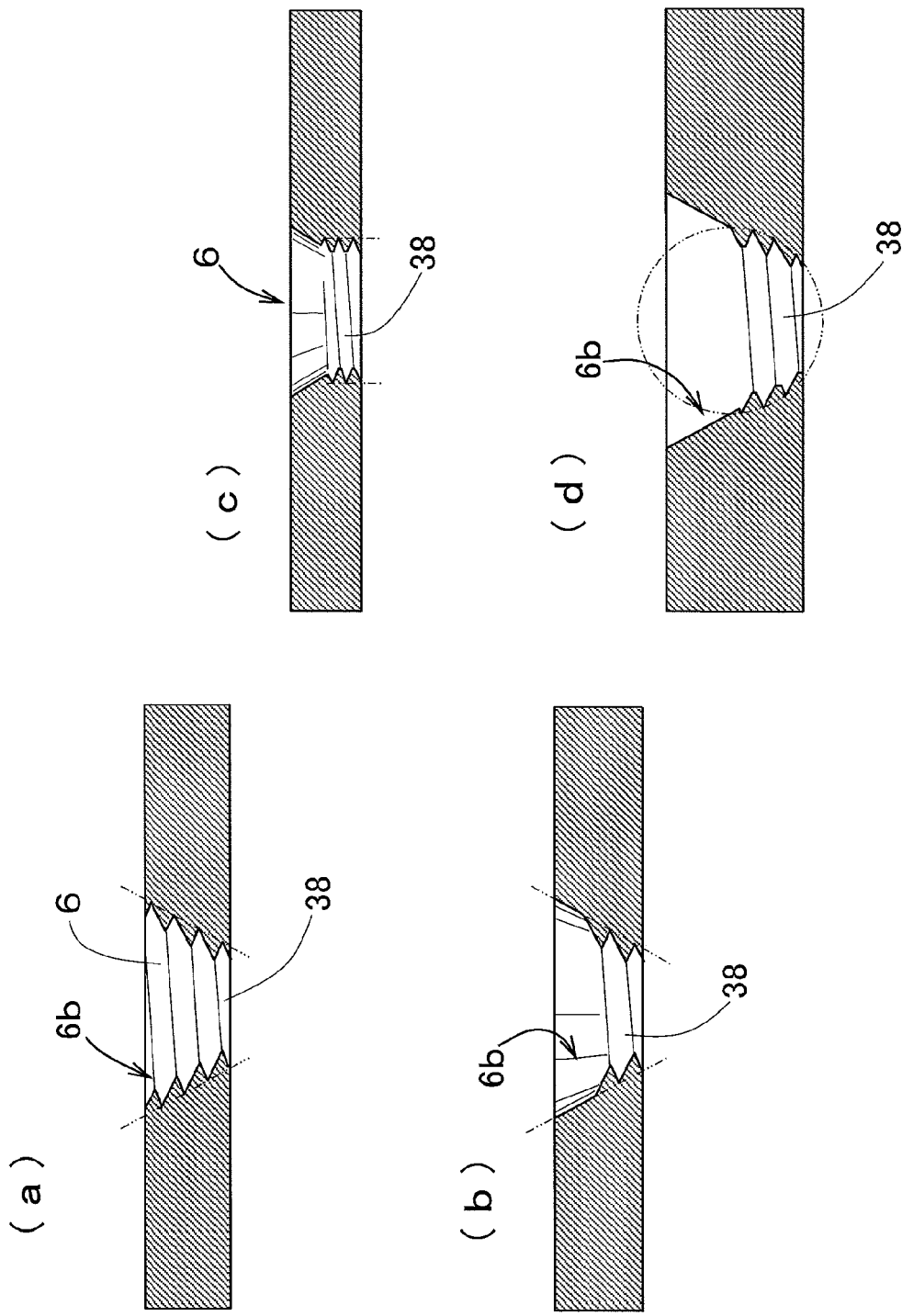
FIG. 19 depicts the state where the whole or a portion of the through-hole has the reverse conical frustum shape.

When the through-hole has the reverse conical frustum shape in its entirety, as depicted in FIGS. 19(a) and 19(c), the circumferentially continuous thread 38 can be formed in the entirety or in the lower half portion of the through-hole. The lower half portion continued from the opening 6b having the reverse conical frustum shape can be formed to have a cylindrical shape as depicted in FIG. 16(d) or the circumferentially continuous thread 38 can be formed as depicted in FIG. 19(c). The opening having the reverse conical frustum shape is oversized relative to the auxiliary thread while the lower half portion of any through-hole is undersized relative to the auxiliary thread and the diameter thereof is increased by the advancement of the auxiliary thread.

For any through-hole, the auxiliary thread taps the threaded hole that has a substantially small back clearance using the self-tapping action whose torque is gradually increased against the hole-defining wall face. The partial undersize of the through-hole creates the restraint state of the desired strength reducing the increase of the torque. Similarly to the case of FIGS. 9(c) and 9(d) of, the self-tapping action of the screw anchor enables the advancement that is inclined against the axis line of the reverse conical frustum through-hole.

This facilitates the pulling of the fractured bone piece to the convenient direction and the fine adjustment of the orientation of the fractured bone piece. When the circumferentially continuous thread is tapped, the advancement of the auxiliary thread creates the restraint state of the desired strength reducing the increase of the torque.

The upper portion of the through-hole is widened, as depicted in FIG. 18(d), so that the accommodation of the head portion 12 of the screw anchor is also excellent and an increase of the created angle is facilitated. The increase of the torque for operation is reduced and the fine adjustment of the fractured bone piece to the desired state is executed, and effects are achieved such as avoidance of employment of any intermittent thread and avoidance of the necessity of any screw insert.

The examples depicted in FIGS. 15(b) and 15(c) are each the example where the enveloping surface of the tooth tips lining on and beneath the auxiliary thread 13 is set to have a partially spherical shape. In the former case, a center 40 of the lower half spherical face is present on the axis line 5a of the screw anchor and, in the latter case, a center 40A is positioned in the anchor but is out of the axis line. Though not depicted, the sphere center can be selected to be positioned out of the anchor.

Figure 20:
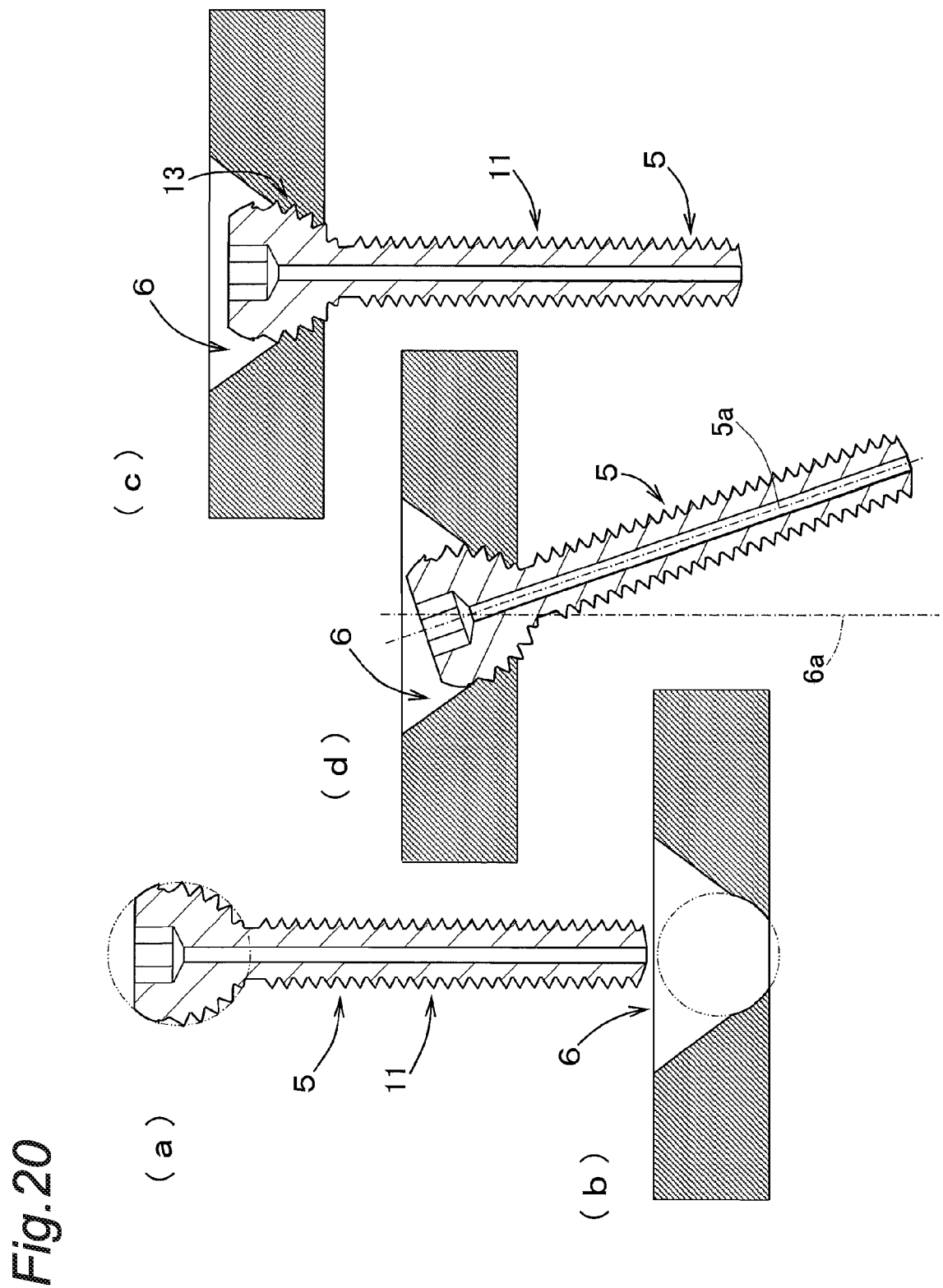
FIG. 20(a) is a cross-sectional diagram of the screw anchor whose enveloping surface of the tooth tips lining on and beneath the screw anchor forms a partially spherical shape.
FIG. 20(b) is a cross-sectional diagram of the radius locking plate whose through-hole upper half portion has the reverse conical frustum shape and whose through-hole lower half portion has a partially spherical shape.
FIG. 20(c) is a cross-sectional diagram of the screw anchor screw-fixed to and not inclined against the radius locking plate.
FIG. 20(d) is a cross-sectional diagram of the screw anchor screw-fixed to and inclined against the radius locking plate.

In this case, the lower half portion of the through-hole may be set to have a partial spherical face as depicted in FIG. 20(b) or a thread may be tapped on this face. As depicted in FIGS. 20(c) and 20(d), the spherical enveloping surface-like screw teeth achieve the desired restraint suppressing any rapid increase of the torque during the use of the self-tapping action for the radius locking plate. The spherical face further increases the degree of freedom of the advancement direction.

The screw anchor cannot use the self-tapping action for the metal radius locking plate. In the present invention utilizing the relation between a metal and a non-metal, the self-tapping is however used. The inventors assured that no problem arose in securing the initial screw-fixation strength and in the change over time of the strength using a bending strength test acted on the screw anchor, or the like. For example, the principal thread was bent of the screw anchor screw-fixed to the circumferentially continuous thread.

No problem arose when the bending was bending in the direction of an arrow 41 in FIG. 21(d) even in the case where the axis line of the auxiliary thread 13 matched with that of the through-hole 6 as depicted in FIG. 21(b) or even in the case where the axis line of the auxiliary thread 13 did not match with that of the through-hole 6 as depicted in FIG. 21(c). The case where a problem arose was the case where bending in the direction of an arrow 42 in FIG. 21(d) was applied. This was the bending in the direction to fill up a gap 43 formed between the circumferentially continuous thread and the auxiliary thread.

Any bending-back against the bending however cannot occur during the surgical operation and after the surgical operation. When one screw anchor is advanced being inclined, the presence is indispensable of other screw anchors firmly standing for (applying counter-forces to) each other. As a result, any degradation of the strength due to the bending-back can therefore be ignored. It was assured that any bending in each of the directions other than this, that is, the directions approaching the reader and leaving the reader that are perpendicular to the page surface including the arrow 41 caused no problem.

Figure 21:
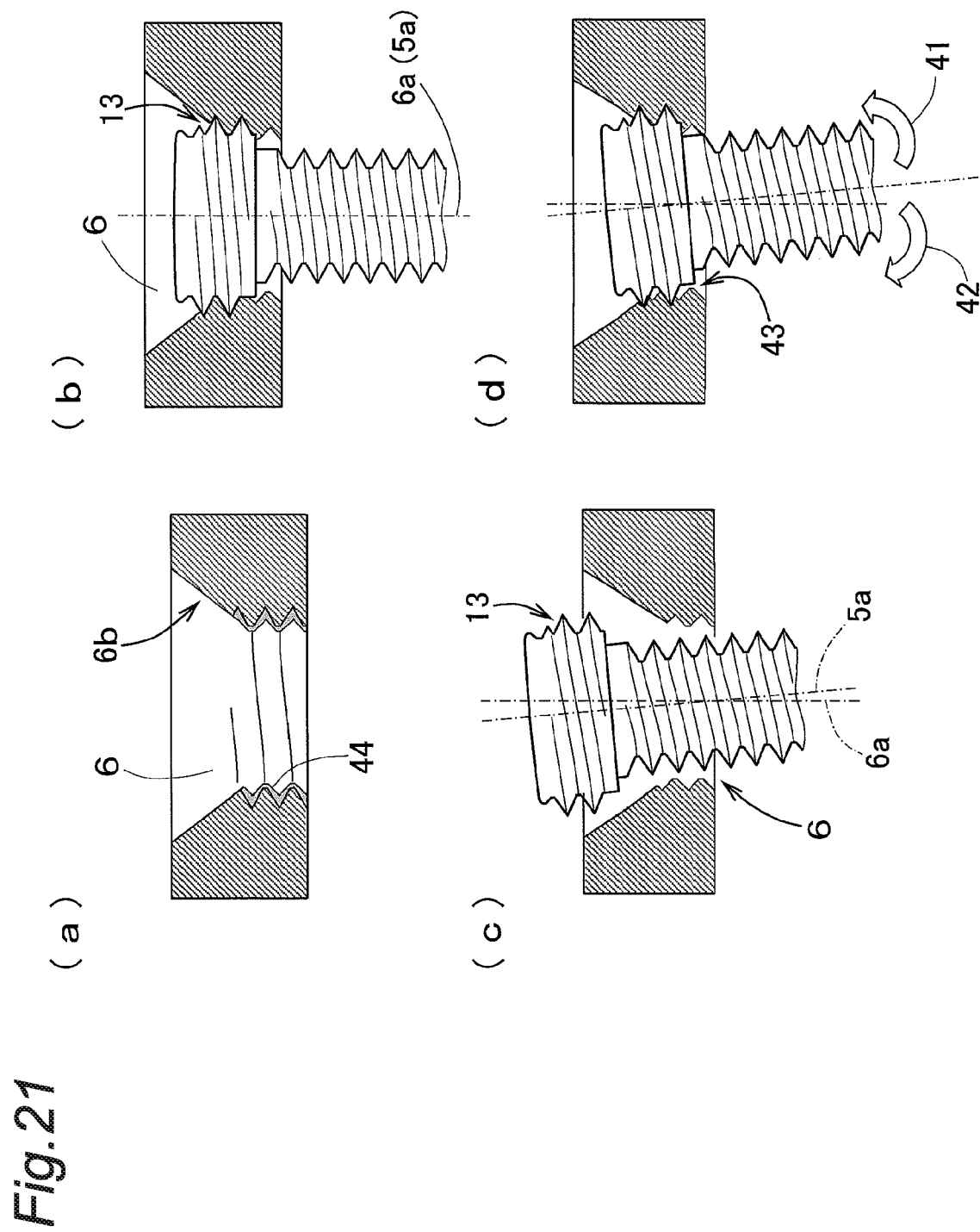
FIG. 21(a) is a partial cross-sectional diagram of the plate of the portion pressed to be hardened when the diameter of the circumferentially continuous thread in the lower half portion is to be increased by the auxiliary thread.
FIG. 21(b) is a diagram of the screw anchor screw-fitted to the circumferentially continuous thread that has a diameter to be increased by the auxiliary thread.
FIG. 21(c) is a diagram of the state of the screw anchor where the auxiliary thread of the screw anchor screw-advancing in the radius inclined against the axis line of the through-hole faces the circumferentially continuous thread before increasing the diameter thereof.
FIG. 21(d) is a diagram of the state of the screw anchor where the auxiliary thread maintaining its inclination against the axis line of the through-hole is screw-fitted to the circumferentially continuous thread increasing the diameter thereof.
Figure 22:
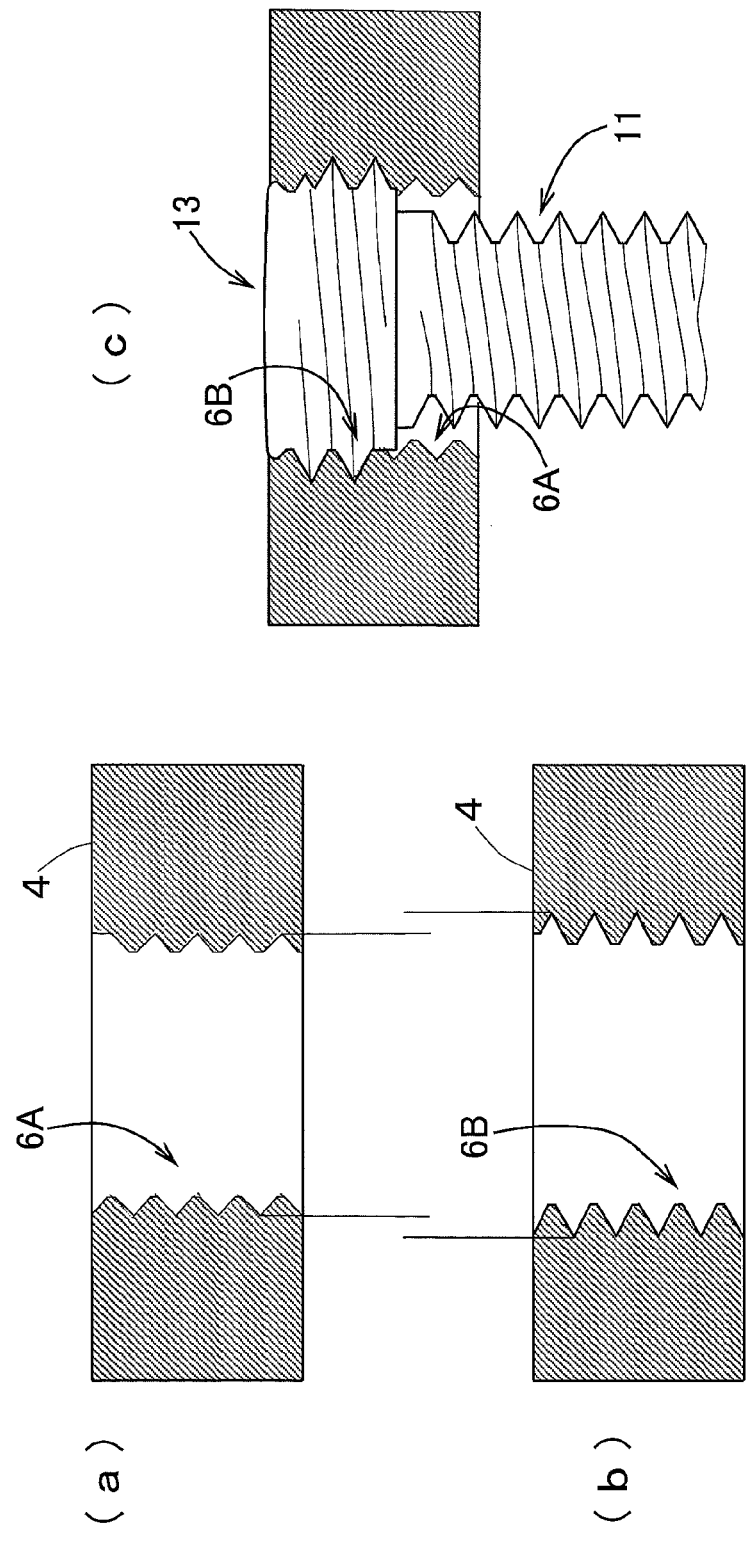
FIG. 22(a) is a cross-sectional diagram of the through-hole before the diameter of the circumferentially continuous thread in the entirety of the through-hole is increased by the auxiliary thread.
FIG. 22(b) is a cross-sectional diagram of the through-hole after the diameter of the circumferentially continuous thread in the entirety of the through-hole is increased by the auxiliary thread
FIG. 22(c) is a diagram of the advancement of the screw anchor in the state where the diameter of the upper half portion of the circumferentially continuous thread is increased by the auxiliary thread and that of the lower half portion is not yet increased.

The increase of the diameter of the undersized thread formed in the through-hole by the auxiliary thread will be described. It is assumed that the auxiliary thread has the cylindrical shape. FIG. 22(a) depicts an undersized threaded hole 6A. FIG. 22(b) depicts a threaded hole 6B that has a diameter increased. FIG. 22(c) depicts the state where the auxiliary thread 13 is advanced to the middle of the threaded hole 6A and the diameter of the lower half portion is not yet increased. FIG. 21 depicts an example of the case where the opening 6b of the through-hole has a reverse conical frustum shape. A shaded portion 44 disappears by the increase of the diameter of the threaded hole as depicted in FIG. 21(a) while the hole-defining wall becomes substantially packed by the auxiliary thread.

Figure 23:
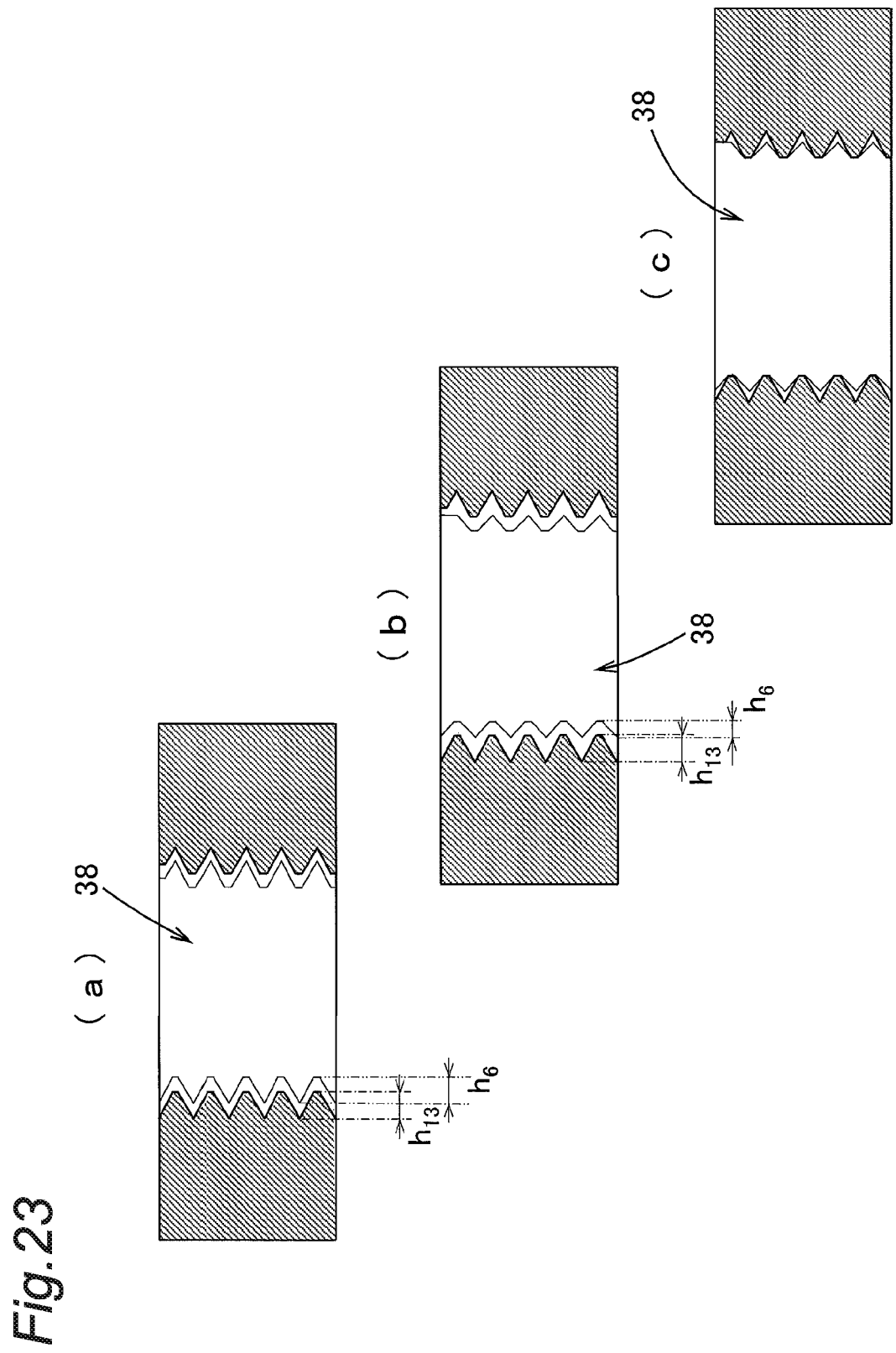
FIG. 23 depicts the undersize of the circumferentially continuous thread.

FIG. 23 depicts the forms of the undersize of the circumference direction continuous screw 38. In both of FIGS. 23(a) and 23(b), the valley-bottom diameter and the inner diameter of the threaded hole after the increase of the diameter are both increased relative to those before the increase of the diameter indicated by thin lines. Not to mention, the pitch of the undersized threaded hole is imparted to be equal to the pitch of the auxiliary thread while, in FIG. 23(a), a height $h_6$ of the thread of the undersized hole is equal to a height $h_{13}$ of the thread of the auxiliary thread. In FIG. 23(b), the height $h_6$ of the thread of the undersized threaded hole is lower than the height $h_{13}$ of the thread of the auxiliary thread. The volume removed by the increase of the diameter is larger in the case of FIG. 23(b) than that in the case of FIG. 23(a).

FIG. 23(c) depicts the case where the inner diameters are equal to each other, and the valley-bottom diameter after the increase of the diameter is larger than that before the increase of the diameter, indicated by the thin lines. The difference in the removed volume is caused only by the difference in the height. Which one of FIGS. 23(a), 23(b), and 23(c) is employed is determined according to the physical properties such as the hardness and the viscosity, and the amount of the reinforced carbon fibers of the resin of the radius locking plate.

FIG. 16(b) depicts an example where a PEEK resin is coated on the surface of the principal thread 11 of the screw anchor (a coating resin 45 is depicted in a dilute color). This is applicable to any of the screw anchors while, after fully examining the state of the radius, this coating only has to be used, for example, for advancement and screw-fixation at the points at which soft touch is necessary. The resin-coated metal teeth of the screw anchor reduce the advancement load on the radius, and any breakage and any destruction of the cortical bone is alleviated. The restrain with the cancellous bone and that with the cortical bone is weaker than that of the naked metal screw while the load of the after-the-fact removal operation is alleviated.

Figure 24:
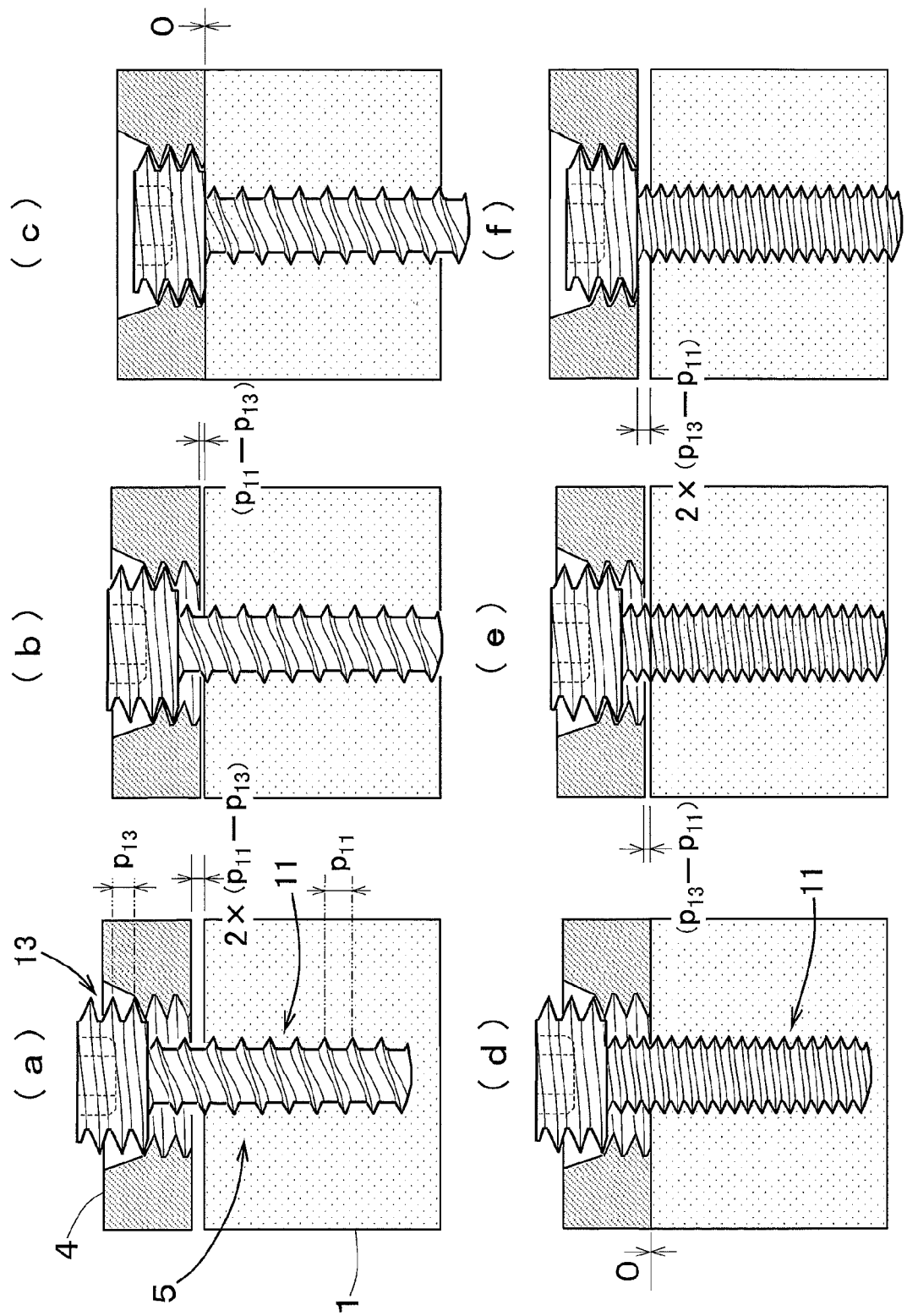
FIGS. 24(a) to 24(c) are explanatory diagrams of the state where the radius locking plate is placed to be adjacent to the radius when the screw anchor is advanced whose thread pitch of the principal thread is larger than the thread pitch of the auxiliary thread.
FIGS. 24(d) to 24(f) are explanatory diagrams of the state where the radius locking plate is disengaged from the radius when the screw anchor is advanced whose thread pitch of the principal thread is smaller than the thread pitch of the auxiliary thread.

FIGS. 24(a) to 24(c) depict an example where a thread pitch $p_{11}$ of the principal thread 11 is set to be larger than a thread pitch $p_{13}$ of the auxiliary thread 13. FIGS. 24(d) to 24(f) depict an example where the thread pitch $p_{11}$ of the principal thread 11 is set to be smaller than the thread pitch $p_{13}$ of the auxiliary thread 13. In the former case, the resin plate can be attached to be adjacent to the radius by the advancement of the screw anchor and, in the latter case, the resin plate can be disengaged from the radius by the advancement of the screw anchor. In the examples described herein, the auxiliary thread of the screw anchor has a constant diameter while the examples are applicable to the case of the gradually reduced diameter described referring to FIG. 15(a).

Description will be made referring to FIGS. 24(a) to 24(c) in this order. When the screw anchor 5 is rotated by, for example, one round, the principal thread 11 advances by one pitch relative to the radius 1. Due to the displacement by the one pitch of the radius locking plate 4 relative to the auxiliary thread 13 of the advanced screw anchor, the radius locking plate makes an approach to the radius by the amount acquired by subtracting the one pitch of the auxiliary thread from the one pitch of the principal thread ($=p_{11}-p_{13}$). This is advantageous to facilitate tight attachment at a position at which the resin plate in its bridging state partially floats from the radius.

In FIGS. 24(d) to 24(f), when the screw anchor rotates by one round, the principal thread advances by one pitch relative to the radius. Due to the displacement by the one pitch of the radius locking plate relative to the auxiliary thread of the advanced screw anchor, the radius locking plate makes disengagement relative the radius by the amount acquired by subtracting the one pitch of the principal thread from the one pitch of the auxiliary thread ($=p_{13}$-$p_{11}$). This facilitate the disengagement at a position at which the resin plate in its bridging state is attached too closely to the radius, and can cause any blood flow disorder of the capillary blood vessels of the periosteum to tend to be avoided by the alleviation of the close attachment.

Figure 25:
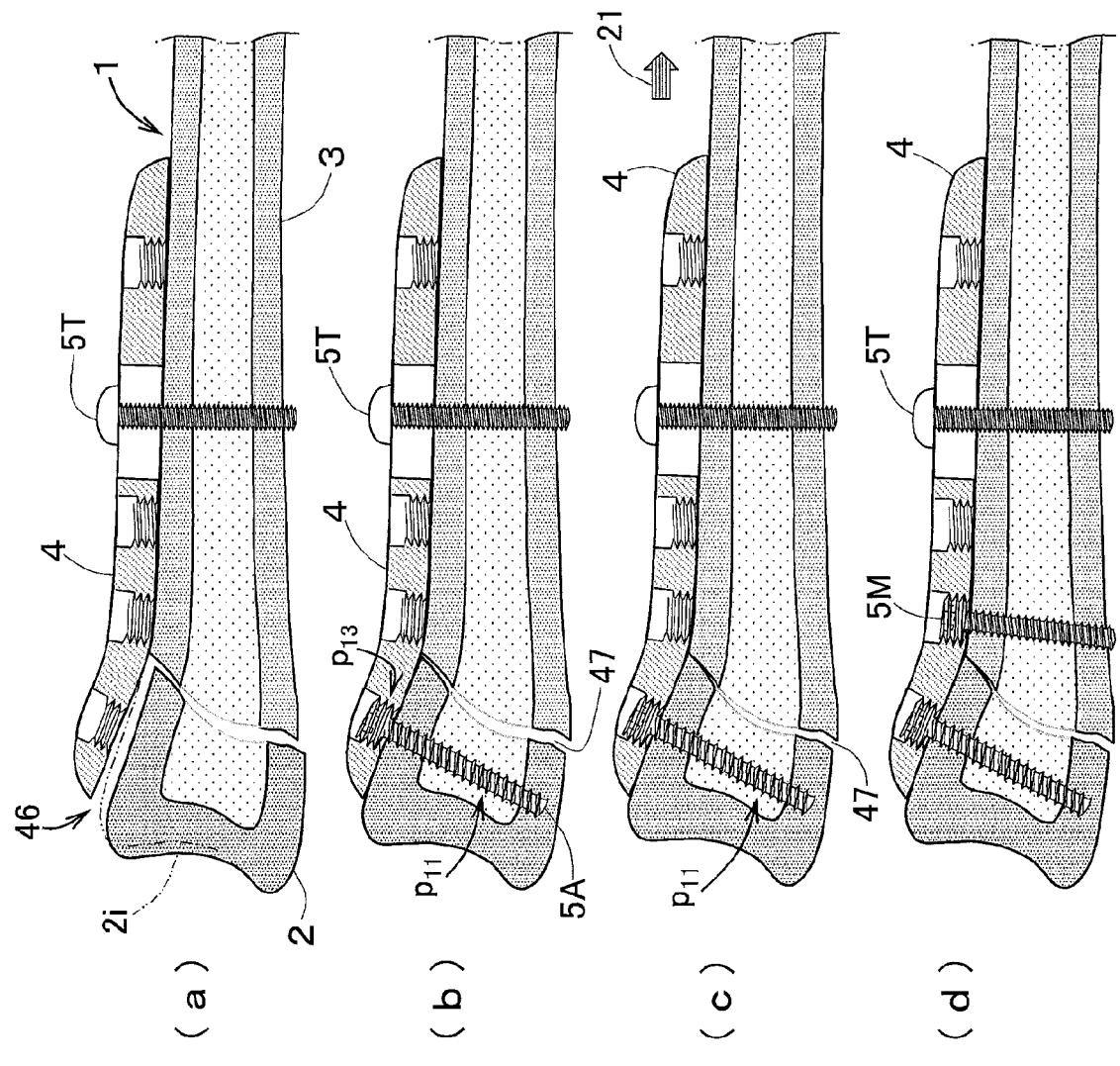
FIG. 25 is a diagram of a fixation process for the radius locking plate, depicted exaggerating a gap that remains in the distal end.
Figure 26:
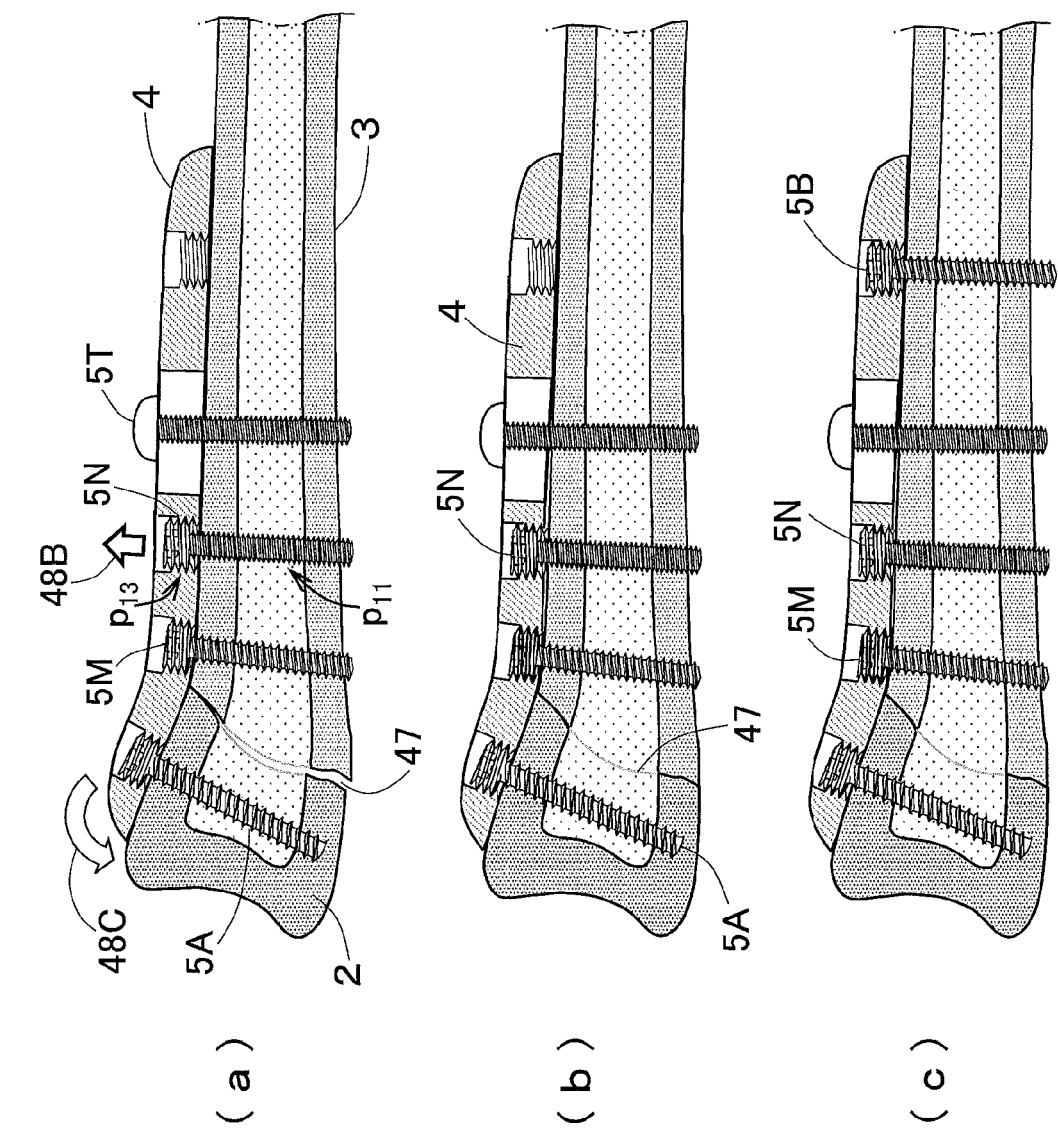
FIG. 26 is a diagram of the fixation process continued from that of FIG. 25.
Figure 27:
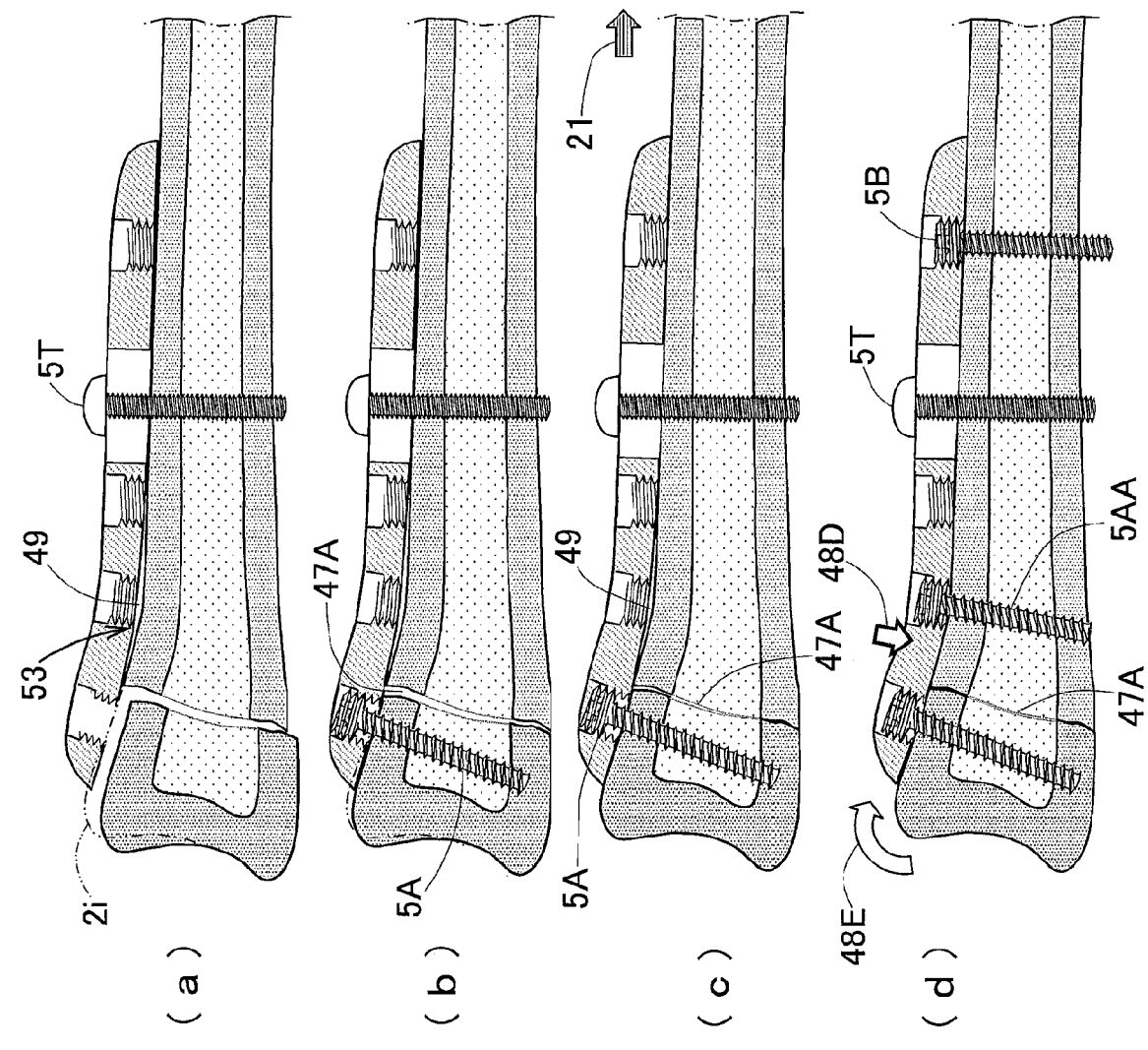
FIG. 27 is a diagram of the fixation process for the radius locking plate, depicted exaggerating a gap in the teardrop recess.

Exemplary one of examples of the former is depicted in FIG. 25 and FIG. 26 and that of the latter is depicted in FIG. 27. All the thread pitches each in the hole having the thread tapped therein only have to be set to be same that each are $p_{13}$ for the through-holes of the radius locking plate. The size of the thread pitch p11 of the principal thread of the screw anchor only has to be the one selected based on the determination by the operator.

FIG. 25 and FIG. 26 depict an example of the procedure for fixing the radius locking plate 4, depicted to exaggerate the gap remaining in the distal end. FIG. 25(a) is a diagram of tentative clamping depicting the state where an excessive bending gap 46 appears between a virtual recovered fractured bone piece 2i and the distal end of the radius locking plate 4 attached to the radius main body 3 due to the screw-fixation of a tentatively clamping screw 5T.

FIG. 25(b) is a diagram of lifting up of the fractured bone piece 2 by the screw anchor 5A including the principal thread having the thread pitch $p_{11}$ that is larger than the thread pitch $p_{13}$ of the auxiliary thread. In this case, the fractured bone piece is closely attached to the radius locking plate and the excessive bending gap disappears while a fracture gap 47 at a position becomes widened as the position becomes more distant from the radius locking plate.

FIG. 25(c) depicts the state where the fractured bone piece 2 is pulled toward the radius main body 3 by somewhat moving the tentatively clamped radius locking plate toward the elbow of a white arrow 21. FIG. 25(d) depicts the state where the vicinity of the through-hole is loosely fixed to the radius main body 3 by driving the screw anchor 5M into the radius main body at the position closest to the fractured bone piece, and the tentatively clamping screw 5T is also somewhat loosened as necessary.

In FIG. 26(a), the radius locking plate 4 is caused to partially be disengaged from the radius 1 in a direction of an arrow 48B by a screw anchor 5N including the principal thread having the thread pitch $p_{11}$ that is smaller than the thread pitch $p_{13}$ of the auxiliary thread screw-advancing in another through-hole close to the elbow. The distal end of the radius locking plate using a screw anchor 5M closest to the fracture bone piece as the fulcrum swivels in a direction of an arrow 48C. FIG. 26(b) is a diagram of substantial leveling of the fracture gap 47. FIG. 26(c) is a diagram of the locking completion state where the necessary number of other screw anchors 5B are fixed in the radius locking plate.

FIG. 27 depicts an example of the procedure for fixing the radius locking plate 4, depicted exaggerating the gap at the teardrop recess. FIG. 27(a) is a diagram of tentative clamping state where an insufficient-bending gap 49 remains at the teardrop recess 53 in the radius locking plate 4 attached to the radius main body 3 due to the screw-fixation of the tentatively clamping screw 5T.

FIG. 27(b) is a diagram of lifting up of the fractured bone piece by the screw anchor 5A including the principal thread having the thread pitch that is larger than the thread pitch of the auxiliary thread and, in this case, a fracture gap 47A becomes widened at a position as the position becomes closer to the radius locking plate when the fractured bone piece is closely attached to the radius locking plate. FIG. 27(c) is a diagram of the state where the fractured bone piece 2 is pulled toward the radius main body 3 to shrink the fracture gap 47 in its entirety by moving the tentatively clamped radius locking plate toward the elbow of the white arrow 21.

FIG. 27(d) is a diagram of swiveling of the distal end of the radius locking plate by closely attaching the radius locking plate to the radius by the advancement of a screw anchor 5AA including the principal thread having the thread pitch larger than the thread pitch of the auxiliary thread in the through-hole in the portion having the insufficient-bending gap 49 remaining therein. The close attachment in a direction of an arrow 48D causes the swivel in a direction of an arrow 48E to substantially level the fracture gaps 47A. The desired number of other screw anchors 5B are fixed to the radius locking plate to complete the locking.

It can be seen that the fitting property of the radius locking plate for the radius can be improved by the above operation. The operation causes bending of the radius locking plate using the advancement, and this bending is an impossible behavior by any metal plate. As repeatedly described, compared to any metal radius locking plate, as to the resin radius locking plate, any deformation at the desired point can be coped with by the advancement operation of the thread and by the after-the-fact heating to deform a lined-up product as above and it is therefore understood that the flexibility thereof is beyond comparison with that of any metal plate. Though the above operation is more meaningful in the case of a fracture of the ulna, the details thereof will not be described.

Figure 28:
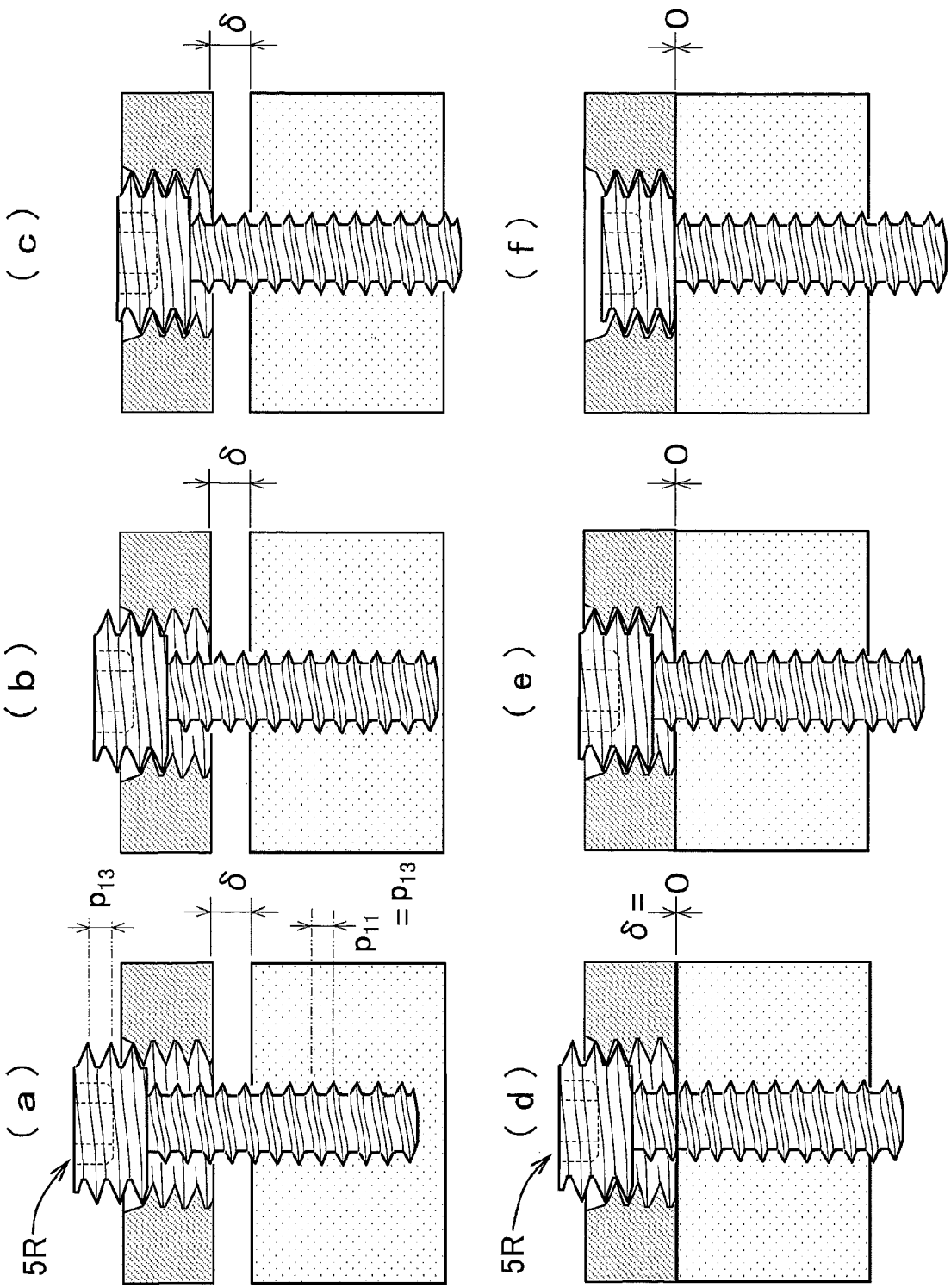
FIG. 28 is an explanatory diagram of the state where the radius locking plate is not displaced relative to the radius when the screw anchor is advanced whose thread pitch of the principal thread is equal to the thread pitch of the auxiliary thread.
Figure 29:
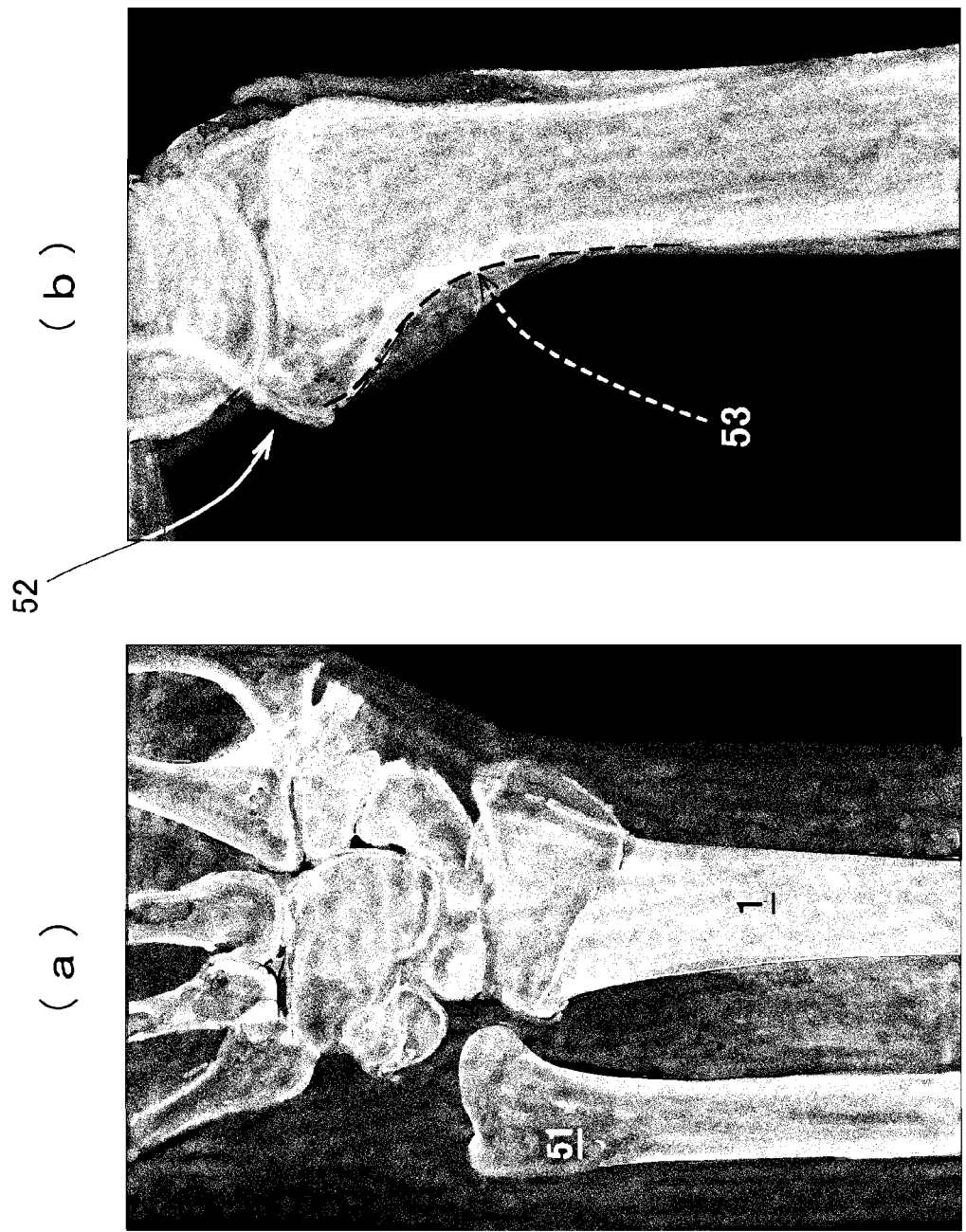
FIG. 29(a) is an X-ray image of a wrist region seen from the palmer side of the right hand and FIG. 29(b) is an X-ray image of the recess.
Figure 30:
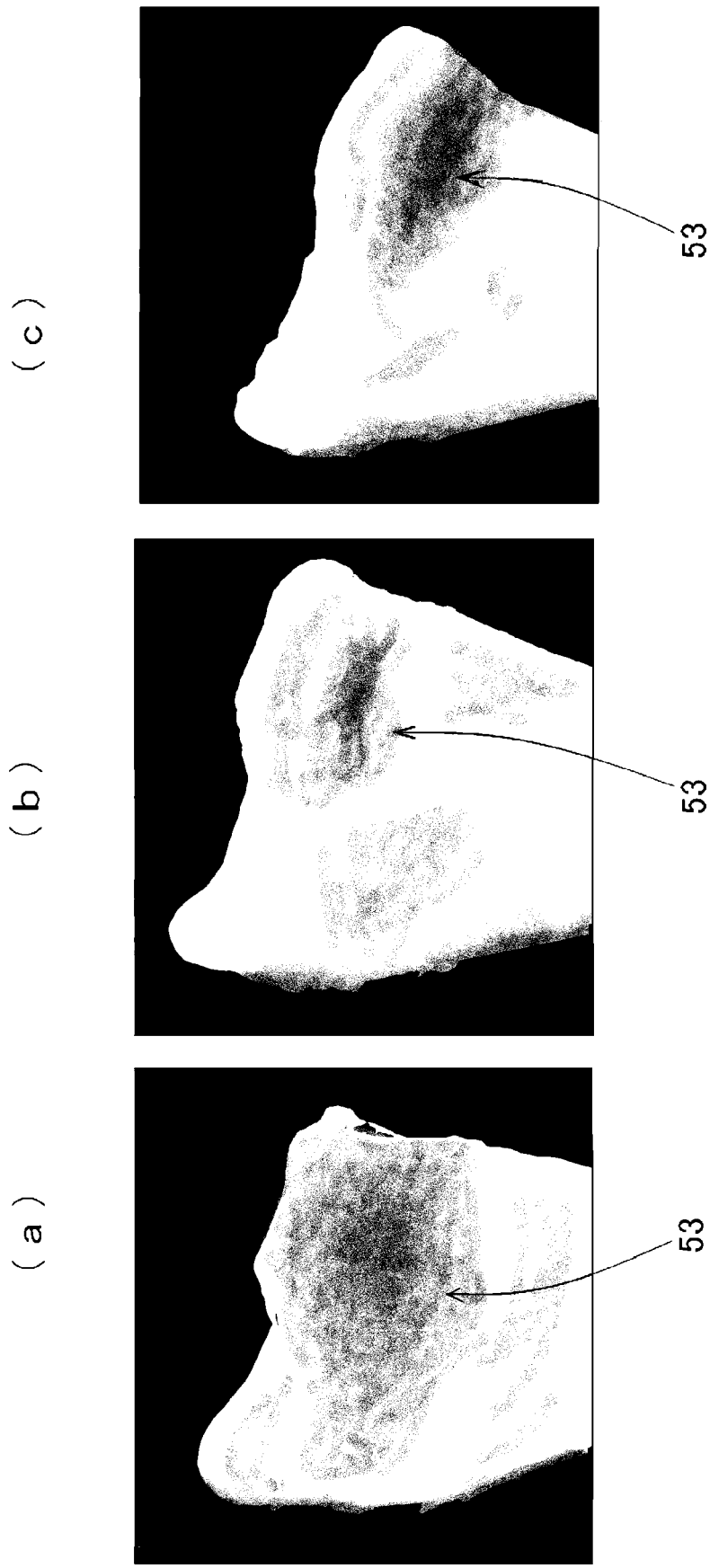
FIG. 30 is a diagram of the shape of a bone end indicating presence of the individual difference in the recess on the palmer side due to the protrusion or the like in the lunate bone fossa of the bone end on the distal side of the radius.
Figure 32:
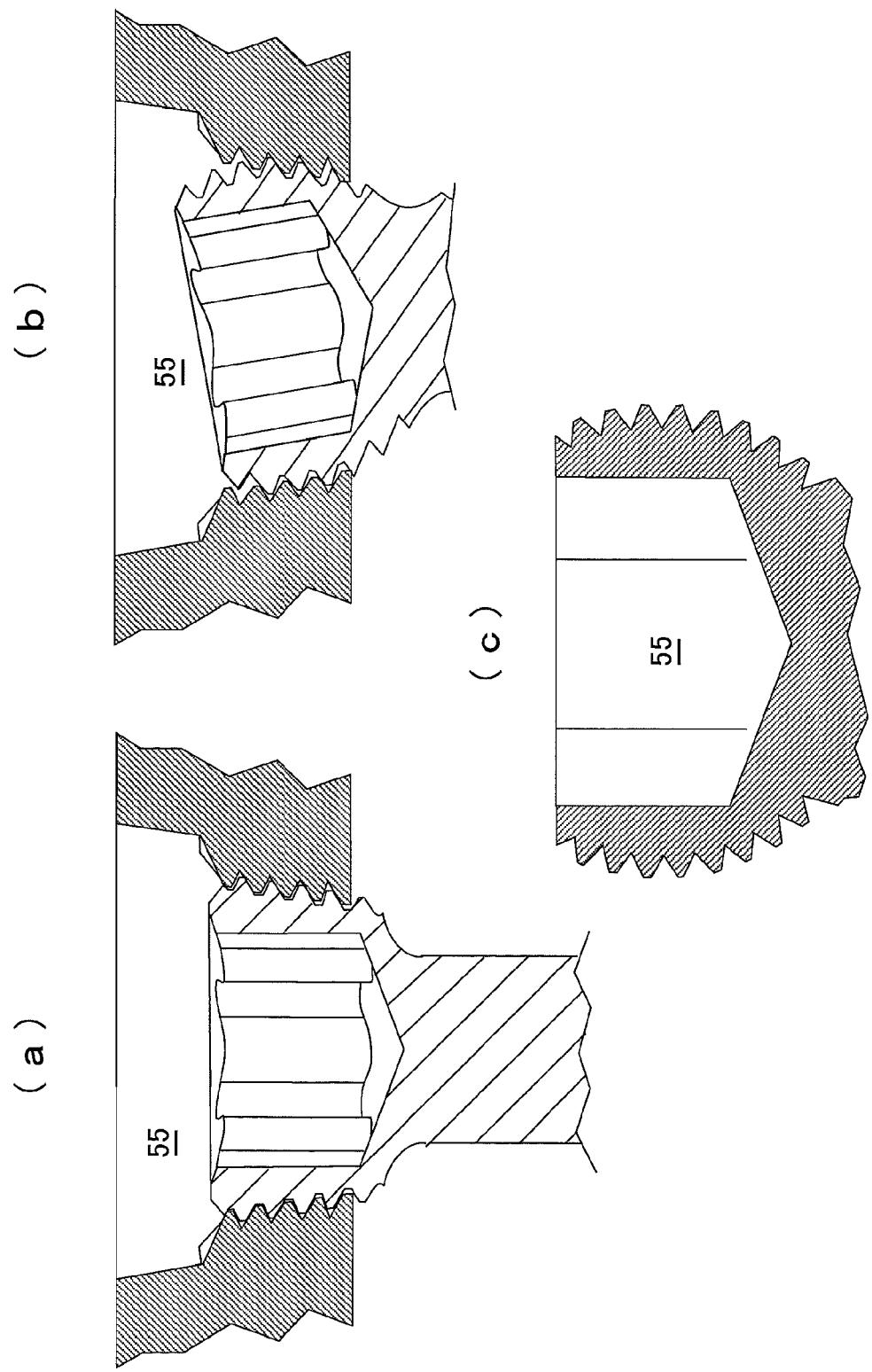
FIG. 32 discloses cross-sectional diagrams of an example of a prior art proposal according to which the enveloping surface of the tooth tips lining on and beneath the auxiliary thread is formed to be a partial spherical face and the enveloping surface of the tooth tips of the thread of the lower half portion of the through-hole is also formed to be a partial spherical face.

As depicted in FIG. 28, with a screw anchor 5R whose principal thread 11 has the thread pitch $p_{11}$ that is equal to the thread pitch $p_{13}$ of the auxiliary thread 13 thereof, even when the screw anchor advances, no behavior is executed to widen or narrow a facing gap δ between the radius locking plate and the radius. In the examples of FIG. 25 and FIG. 27, this is applicable to the screw anchors 5M and 5B.

The elements and the combinations thereof described in the present invention will additionally be described. The elements will be simply denoted by a letter "C" and a subsequent three-digit number.

C011: The radius locking plate is a flat laminate of intermediate molding materials each including carbon fibers as reinforcing material and thermoplastic resin as a matrix.

C012: The screw anchor is made of hard metal and the shaft portion thereof has a principal thread achieving a self-tapping action formed thereon while the outer circumference of the head portion thereof also has an auxiliary thread achieving a self-tapping action tapped thereon.

C013: The diameter of a through-hole in the radius rocking plate to fix the radius main body and a fractured bone piece is oversized relative to the principal thread and is undersized in the through-hole in its entirety or in the lower half portion relative to the auxiliary thread.

C021: The intermediate molding material reinforced by the carbon fibers of the 45°-orientation material or the ±45°-orientation woven cloth is used in the upper layers and the lower layers of the radius locking plate, and intermediate molding materials each reinforced by the carbon fibers of a one-direction material or a 0°/90°-orientation woven cloth are used in the intermediate layer.

C031: The through-hole has the cylindrical shape.

C041: The cylindrical through-hole is oversized in the upper half portion thereof relative to the principal thread and is undersized in the lower half portion thereof relative to the auxiliary thread.

C051: The cylindrical through-hole has a circumferentially continuous thread that has a diameter to be increased by the auxiliary thread, tapped in the through-hole in its entirety or in the upper half portion thereof.

C061: The through-hole has a reverse conical frustum shape in at least its opening.

C071: The lower half portion of the through-hole has a cylindrical shape and has a diameter increased by the auxiliary thread.

C081: The lower half portion of the through-hole has the circumferentially continuous thread tapped therein that has a diameter to be increased by the auxiliary thread.

C091: The through-hole has a reverse conical frustum shape in its entirety, and the through-hole has a circumferentially continuous thread tapped in its entirety or its lower half portion, the circumferentially continuous thread has a diameter to be increased by the auxiliary thread.

C101: The lower half portion of the through-hole has a partially spherical shape.

C111: The auxiliary thread has an enveloping surface of the tooth tips lining thereon and therebeneath forming a partially spherical shape.

C121: The auxiliary thread has an enveloping surface of the tooth tips lining thereon and therebeneath forming a reverse conical frustum shape.

C131: A PEEK resin is coated on the surface of the principal thread of the screw anchor.

C141: The thread pitch of the principal thread is larger than the thread pitch of the auxiliary thread of the screw anchor.

C151: The thread pitch of the principal thread is smaller than the thread pitch of the auxiliary thread of the screw anchor.

C161: A metal wire tracing the contour of the radius locking plate is embedded in the edge portion of this plate.

C171: An intermediate molding material is coated to the face on the radius counter-approximal face of the flat laminate of the intermediate molding materials.

C181: A non-reinforced resin is applied to the face on the radius counter-approximal face of the flat laminate of the intermediate molding materials.

C191: The non-reinforced resin is applied to the face on the radius approximal face of the radius locking plate.

C201: Small protrusions are provided on the face on the radius approximal face of the radius locking plate.

C211: To provide the small protrusions, the positions corresponding to the small protrusions of the flat laminate are defined by a PEEK resin compound layer.

C221: The lateral cross-sectional shape of the radius locking plate is set to be a substantially crescent shape.

C231: The bending of the radius locking plate is provisionally set and typical plural radius locking plates having different lengths and different widths are lined up as semi-finished products.

C241: A finished product of the radius locking plate is a bending-corrected product that is formed by partially heating the semi-finished product to adapt the distal portion point thereof to the teardrop recess of the radius for application.

The elements and the combinations thereof described in the present invention are also realized in the following cases.

[1] Addition of any one element or a combination of any plural elements of C121, C131, C141, C151, C161, C171, C181, C191, and C201 to an invention including C011, C012, and C013 (hereinafter, collectively referred to as "C01T") and C021 (hereinafter, collectively referred to as "C12-20T").

[2] Addition of C12-20T also to an invention that includes C01T, C021, and C031.

[3] Addition of C10-20T also to an invention that includes C01T, C021, C031, and C041.

[4] Addition of C12-20T also to an invention that includes C01T, C021, C031, and C051.

[5] Addition of C12-20T to an invention that includes C01T, C021, and C061.

[6] Addition of C12-20T also to an invention that includes C01T, C021, C061, and C071.

[7] Addition of C12-20T also to an invention that includes C01T, C021, C061, C071, and C081.

[8] Addition of C12-20T to an invention that includes C01T, C021, C061, and C091.

[9] Addition of C12-20T to an invention that includes C01T, C021, C061, and C101.

[10] Addition of C12-20T to also an invention that includes C01T, C021, C061, C101, and C111.

[11] Addition of C211 to an invention that includes C01T, C021, and C201.

[12] Addition of C12-20T and/or C211 also to an invention that includes C01T, C021, and C221.

The invention claimed is:

1. A locking plate system for treatment of a distal radius fracture comprising:

a radius locking plate to be attached as a bridge between a fractured bone piece and a palmer side of a radius main body for recovering a position and an orientation of the fractured bone piece produced at a distal radius or in a vicinity thereof and subsequently enhance bone union of the fractured bone piece and the radius main body, wherein the radius locking plate is a laminate of layers that each include carbon fibers as a reinforcing material and thermoplastic resin as a matrix, wherein the radius locking plate includes a radius approximal face, a radius counter-approximal face and a through-hole, wherein the radius locking plate has a lateral cross-section that is substantially crescent shaped, and wherein a plane on the radius approximal face and a plane on the radius counter-approximal face intersect at an edge of the radius locking plate at an angle equal to or smaller than 40°; and a screw anchor used for the radius locking plate, wherein the screw anchor is made of hard metal and includes a shaft portion and a head portion, wherein the shaft portion has a principal thread formed thereon and an outer circumference of the head portion has an auxiliary thread tapped thereon, and wherein a diameter of the through-hole in the radius locking plate, which allows the radius main body and the fractured bone piece to be threadably fixed to the radius locking plate, is oversized relative to the principal thread.

2. The locking plate system for treatment of a distal radius fracture according to claim 1, wherein the layers include upper and lower layers reinforced by carbon fibers having a 45°-orientation material or a ±45°-orientation woven cloth, and a further intermediate layer between the upper and lower layers reinforced by carbon fibers of a one-direction material or a 0°/90°-orientation woven cloth.

3. The locking plate system for treatment of a distal radius fracture according to claim 1, wherein the through-hole has a cylindrical shape.

4. The locking plate system for treatment of a distal radius fracture according to claim 3, wherein the cylindrical through-hole is oversized in an upper half portion thereof and is undersized in a lower half portion thereof, relative to the auxiliary thread.

5. The locking plate system for treatment of a distal radius fracture according to claim 3, wherein the cylindrical through-hole has a circumferentially continuous thread tapped in its entirety or its lower half portion, the circumferentially continuous thread having a diameter to be increased by the auxiliary thread.

6. The locking plate system for treatment of a distal radius fracture according to claim 1, wherein the through-hole has a reverse conical frustum shape in at least its opening.

7. The locking plate system for treatment of a distal radius fracture according to claim 6, wherein the through-hole has a cylindrical shape and has a diameter of the lower half portion of the through-hole, the diameter being increased by the auxiliary thread.

8. The locking plate system for treatment of a distal radius fracture according to claim 7, wherein the through-hole has a circumferentially continuous thread that has a diameter to be increased by the auxiliary thread, the circumferentially continuous thread being tapped in the lower half portion thereof.

9. The locking plate system for treatment of a distal radius fracture according to claim 6, wherein the through-hole has a reverse conical frustum shape in its entirety and the through-hole has a circumferentially continuous thread, the circumferentially continuous thread having a diameter to be increased by the auxiliary thread, tapped in an overall hole or a lower half portion thereof.

10. The locking plate system for treatment of a distal radius fracture according to claim 6, wherein the lower half portion of the through-hole has a partially spherical shape.

11. The locking plate system for treatment of a distal radius fracture according to claim 10, wherein an enveloping surface of tooth tips lining on and beneath the auxiliary thread forms a partially spherical shape.

12. The locking plate system for treatment of a distal radius fracture according to claim 1, wherein an enveloping surface of tooth tips lining on and beneath the auxiliary thread forms a reverse conical frustum shape.

13. The locking plate system for treatment of a distal radius fracture according to claim 1, wherein a PEEK resin is coated on a surface of the principal thread of the screw anchor.

14. The locking plate system for treatment of a distal radius fracture according to claim 1, wherein a thread pitch of the principal thread is larger than a thread pitch of the auxiliary thread of the screw anchor.

15. The locking plate system for treatment of a distal radius fracture according to claim 1, wherein a thread pitch of the principal thread is smaller than a thread pitch of the auxiliary thread of the screw anchor.

16. The locking plate system for treatment of a distal radius fracture according to claim 1, wherein a metal wire tracing a contour of the radius locking plate is embedded in an edge portion of the plate.

17. The locking plate system for treatment of a distal radius fracture according to claim 1, wherein a sheet is coated to a face on the radius counter-approximal face of the laminate.

18. The locking plate system for treatment of a distal radius fracture according to claim 1, wherein a non-reinforced resin is applied to a face on the radius counter-approximal face of the laminate.

19. The locking plate system for treatment of a distal radius fracture according to claim 1, wherein a non-reinforced resin is applied to a face on the radius approximal face of the radius locking plate.

20. The locking plate system for treatment of a distal radius fracture according to claim 1, wherein small protrusions are provided on a face on the radius approximal face of the radius locking plate.

21. The locking plate system for treatment of a distal radius fracture according to claim 20, wherein to provide the small protrusions, positions corresponding to the small protrusions of the flat laminate are defined by a PEEK resin compound layer.

22. The locking plate system for treatment of a distal radius fracture according to claim 1, wherein bending of the radius locking plate is provisionally set, and wherein typical plural radius locking plates having different lengths and different widths are lined up as semi-finished products.

23. The locking plate system for treatment of a distal radius fracture according to claim 22, wherein the finished product of the radius locking plate is a bending-corrected product that is formed by partially heating the semi-finished product to adapt a distal point of the semi-finished product to a teardrop recess of a radius for application.

* * * * *